(12) United States Patent
Hynynen et al.

(10) Patent No.: US 7,344,509 B2
(45) Date of Patent: Mar. 18, 2008

(54) SHEAR MODE THERAPEUTIC ULTRASOUND

(76) Inventors: Kullervo Hynynen, 57 Indian Hill Rd., Medfield, MA (US) 02052; Gregory T. Clement, 2000 Commonwealth Ave. 1603, Boston, MA (US) 02115

(*) Notice: Subject to any disclaimer, the term of this patent is extended or adjusted under 35 U.S.C. 154(b) by 530 days.

(21) Appl. No.: 10/822,019

(22) Filed: Apr. 9, 2004

(65) Prior Publication Data

US 2004/0210134 A1    Oct. 21, 2004

Related U.S. Application Data

(60) Provisional application No. 60/463,589, filed on Apr. 17, 2003.

(51) Int. Cl.
*A61H 1/00* (2006.01)
(52) U.S. Cl. .......................................................... 601/3
(58) Field of Classification Search ................. 600/439; 601/2–4; 606/1; 604/22
See application file for complete search history.

(56) References Cited

U.S. PATENT DOCUMENTS

| | | | |
|---|---|---|---|
| 4,221,132 A | 9/1980 | Poole | 73/620 |
| 4,817,614 A | 4/1989 | Hassler et al. | 128/660.05 |
| 5,197,475 A | 3/1993 | Antich et al. | 128/660.01 |
| 5,520,612 A * | 5/1996 | Winder et al. | 601/2 |
| 5,606,971 A | 3/1997 | Sarvazyan | 128/660.02 |
| 5,728,062 A * | 3/1998 | Brisken | 604/22 |
| 5,752,515 A | 5/1998 | Jolesz et al. | 128/653.1 |
| 5,810,731 A | 9/1998 | Sarvazyan et al. | 600/438 |
| 5,904,659 A * | 5/1999 | Duarte et al. | 601/2 |
| 6,135,960 A | 10/2000 | Holmberg | 600/447 |
| 6,217,530 B1 * | 4/2001 | Martin et al. | 601/2 |
| 6,433,464 B2 * | 8/2002 | Jones | 310/328 |
| 6,524,251 B2 * | 2/2003 | Rabiner et al. | 600/439 |
| 2002/0016557 A1 | 2/2002 | Duarte et al. | 601/2 |
| 2002/0095087 A1 | 7/2002 | Mourad et al. | 600/442 |
| 2002/0161300 A1 | 10/2002 | Hoff et al. | 600/449 |

FOREIGN PATENT DOCUMENTS

| | | |
|---|---|---|
| WO | WO 99/56829 | 11/1999 |
| WO | WO 03/013654 A1 | 2/2003 |
| WO | WO 03/017843 A1 | 3/2003 |

OTHER PUBLICATIONS

International Search Report for PCT/US2004/011374, mailing date: Jul. 21, 2004.
International Search Report for PCT/US04/011378, mailing date: Jul. 20, 2004.

* cited by examiner

*Primary Examiner*—Francis J. Jaworski
(74) *Attorney, Agent, or Firm*—Mintz Levin Cohn Ferris Glovsky and Popeo, PC

(57) ABSTRACT

A method of delivering ultrasound signals using shear waves includes applying a portion of at least a first ultrasound beam to a subject at at least a first incident angle relative to the surface of the subject to induce shear waves in the subject, energy in the shear waves forming a substantial part of energy of first ultrasound waves at a desired region in the subject at a therapeutic level.

31 Claims, 23 Drawing Sheets

Coded Excitation

Coded Excitation – Cross Correlation with X-ducer Response

SHEAR MODE THERAPEUTIC ULTRASOUND

CROSS-REFERENCE TO RELATED ACTIONS

This application claims the benefit of U.S. Provisional Application No. 60/463,589 filed Apr. 17, 2003 and entitled "Transskull Shear Mode Ultrasound" which is incorporated here by reference.

STATEMENT AS TO FEDERALLY-SPONSORED RESEARCH

This invention was made at least in part with Government support under Grant No. NIH CA76550, awarded by the National Institutes of Health. The Government has certain rights in this invention.

FIELD OF THE INVENTION

The invention relates to ultrasound diagnostic and therapeutic applications using shear waves.

BACKGROUND OF THE INVENTION

Since its inception in the early 1980's, transcranial ultrasound Doppler imaging has demonstrated an ability to measure blood flow, hemorrhages, and perfusion in the brain. Recent research has also examined the possibility of diagnosing certain degenerative disorders such as Parkinson's and depression. These approaches use transcranial Doppler sonography (TCD), or the related transcranial color coded sonography (TCCS) to record frequency shifts in the sent and backscattered signals. Signals are generally applied with a relatively low frequency (~2 MHz) probe in order to penetrate the skull bone, and are often used in conjunction with a contrast agent. There seems to be little advantage to applying frequencies above 2 MHz, as the skull's increased attenuation at higher frequencies causes the bone to act as a low pass filter, returning only the lower spectral frequencies. Center frequencies at and below 1 MHz have also been examined, showing a stronger signal intensity, but with an expected reduced resolution.

The primary setbacks for transcranial procedures are strong attenuation and the distortion caused by irregularities in the skull's shape, density, and sound speed. These properties collectively contribute toward destroying an ultrasound focus and/or decreasing the ability to spatially register received diagnostic information.

Coherent noninvasive focusing of ultrasound through the human skull has been suggested for a number of therapeutic and diagnostic implications in the brain. For example, ultrasound has been considered as a tool for the transskull treatment of brain tumors, targeted drug delivery, improved thrombolytic stroke treatment, blood flow imaging, detecting internal bleeding, and tomographic brain imaging. Although the human skull has been the barrier to clinical realization of many of these applications, studies have demonstrated both minimally invasive and noninvasive aberration correction methods for transskull focusing. Minimally invasive approaches use receiving probes designed for catheter insertion into the brain to measure the amplitude and phase distortion caused by the skull and then correct the beam using an array of ultrasound transducers. Alternatively, a completely noninvasive approach uses X-ray computed tomography (CT) images to predict the longitudinal wave distortion caused by the skull. Noninvasive focusing with a therapeutic array has been demonstrated with a longitudinal wave propagation model, but the amplitude of the focus was observed to drop when the focus was directed close to the skull surface.

The assumption that the transcranial propagation is composed of mainly longitudinal modes is valid for small incident beam angles, but rapidly breaks down beyond approximately 25°, as the longitudinal wave approaches its critical angle. This is a plausible explanation for reduced amplitude using the longitudinal model—As the focus is directed toward the periphery of the brain, an increasing number array elements are oriented at higher incident angles to the skull.

Modeling of shear waves has been dismissed as being either of insignificant amplitude or, if significant, that the resulting beam would be incoherent and hard to predict. The absence of significant information on the skull bone's elastic wave speeds also has inhibited its consideration in modeling. Similar issues exist with respect to ultrasound propagation through other bony structures.

SUMMARY OF THE INVENTION

It has been discovered that ultrasound beams can be effectively, coherently transmitted through bone via shear waves. This can be accomplished, for example, by increasing the angle between the beam and the normal to the bone surface beyond the critical angle (approximately 20°) that causes complete reflections of the longitudinal waves. At angles between approximately 25° and 60°, shear waves are generated and propagated through the bone and at the inner surface converted again into longitudinal waves that propagate into the soft tissues on the other side of the bone. This finding has several implications: First, the shear waves have roughly the same propagation velocity in the bone as the longitudinal waves have in soft tissues. Thus, the wave front may not be significantly distorted by the variable thickness of bone as it is for longitudinal waves due to the higher speed of sound in bone (2500-3000 ms/s). It is possible to focus ultrasound beams though bone without performing complex patient-specific aberration corrections. For example, diagnostic ultrasound imaging of the brain can be performed as well as ultrasound brain treatments and diagnosis with relatively simple devices. A second implication is that the entrance angle of the beam can be increased and can reach larger brain volumes with higher gain than using longitudinal waves. Third, predictions of ultrasound focusing through a skull can be significantly improved by combining shear wave propagation modeling with longitudinal propagation models. Further, undesired reflections from bone layers may be reduced or eliminated, making diagnostic information easier to analyze.

Embodiments of the invention may provide one or more of the following capabilities and can be used for one or more of the following uses. The invention can be used in ultrasound diagnosis and/or therapy and can aid methods that rely on transmitting ultrasound through bone. In particular, the invention can be applied to systems that seek to image blood flow through bone, or can be an enhancement/add-on for existing ultrasound imaging and/or therapeutic devices, or in a stand-alone device for transbone ultrasound therapy and/or applied to techniques that rely on opening of the blood-brain barrier (BBB) using ultrasound or any other diagnostic or therapeutic procedures conducted using ultrasound. Focusing of ultrasound could be greatly simplified, and phase distortion correction could be reduced and possibly eliminated. The tissue volume that can be currently reached with ultrasound can be increased. In addition, embodiments of the invention can detect cavities in bony structures and/or detection/determination of cavity contents with undesired reflections from bone surfaces being reduced or eliminated.

In general, in an aspect, the invention provides a method of diagnosing a subject by delivering ultrasound signals using shear waves, the method including applying a portion of an ultrasound mainbeam to a bone surface at an incident angle relative to the surface of the bone to induce shear waves in the bone, energy in the shear waves forming a substantial part of energy of first ultrasound waves at a desired region in the subject through the bone, detecting at least one of reflected and scattered energy of the applied ultrasound mainbeam, and analyzing the detected energy for a diagnostic purpose.

Implementations of the invention may include one or more of the following features. The portion of the ultrasound mainbeam is applied to the bone surface between a longitudinal wave critical angle associated with the subject and a shear wave critical angle associated with the subject. The analyzing includes producing an image of at least a portion of the desired region. The desired region is a linear region along a line of transmission of the ultrasound mainbeam. Applying the portion of the ultrasound mainbeam comprises applying the portion of the ultrasound mainbeam to bone. The bone is a skull, and the portion of the ultrasound mainbeam is directed at the skull at the incident angle in order to reach the desired region within the skull. The desired region is one of a sinus cavity and an inner ear cavity, the method further comprising providing an indication of whether the desired region is at least partially fluid filled. The desired region is one of a tooth and a jaw bone, the method further comprising at least one of: providing an indication of whether the desired region has at least one of a cavity and an abscess, and obtaining an image of at least one of anatomy and blood perfusion of the desired region.

Implementations of the invention may also include one or more of the following features. The at least a first ultrasound mainbeam is applied in multiple pulses of different frequencies. The different frequencies are within a range of frequencies from about 0.3 MHz and about 5 MHz. The different frequencies are within a range of frequencies from about 1 MHz and about 3 MHz. The pulses have durations within a range of about 1 cycle to about 100 cycles. The different pulses have corresponding different amplitudes to compensate for different attenuation amounts associated with the different frequencies. The at least a first ultrasound mainbeam is applied in a burst of multiple cycles, at least two of the cycles having at least one of different frequencies, different phases, and different amplitudes.

In general in another aspect, the invention provides a system for diagnosing a subject by delivering ultrasound signals to a target region in the subject using shear waves, the system including a transceiver configured to transmit ultrasound energy, directing means, coupled to the transceiver, for causing a portion of a mainbeam of the transmitted ultrasound energy to be incident upon a bone surface of the subject such that ultrasound energy in the portion of the mainbeam from the source will induce shear waves in the bone with energy in the shear waves forming a substantial part of energy of ultrasound waves at the target region, and analyzing means, coupled to the transceiver, for analyzing energy from the portion of the mainbeam that is returned from the target region for diagnostic purposes.

Implementations of the invention may include one or more of the following features. The directing means are configured to cause the portion of the mainbeam to be incident upon the bone surface at a first angle between a longitudinal critical angle associated with the bone and a shear critical angle associated with the bone. The directing means comprises at least one of (1) a positioner configured to mechanically direct a normal direction associated with the source toward the surface of the bone at the first angle, (2) a phase/delay adjuster, where the transceiver comprises a plurality of radiating elements, the phase/delay adjuster being configured to regulate at least one of phases and delays of the plurality of radiating elements to electronically steer at least the first mainbeam, and (3) an actuation regulator, where the transceiver comprises a plurality of radiating elements, the actuation regulator being configured to actuate the elements at different times to direct the mainbeam as desired. The positioner is configured to at least one of (1) couple to the subject and the transceiver in a fixed manner such that the normal is directed toward the surface at the first angle, and (2) mechanically adjust the transceiver such that the normal is directed toward the surface at the first angle. The transceiver comprises a plurality of elements configured to radiate ultrasound energy, the system comprising a controller configured and coupled to cause at least a portion of the transceiver to emit ultrasound energy, to process indicia of returned energy due to the emitted energy to determine an orientation of at least a portion of the surface relative to the transceiver, and to actuate only elements of the source that have their mainbeams at least partially directed at the portion of the surface between the longitudinal critical angle and the shear wave critical angle. The controller is configured to process the indicia of returned energy to form an image of the at least a portion of the surface.

Implementations of the invention may also include one or more of the following features. The system includes a controller coupled to the transceiver and configured to actuate the transceiver to produce the mainbeam for transmitting energy to the target region, and the surface of the subject is an outer surface of a skull of the subject. The system includes a controller coupled to the transceiver and configured to actuate the transceiver to produce the mainbeam in a plurality of pulses with different frequencies and amplitudes. The different frequencies are within a range of frequencies from about 0.5 MHz and about 5 MHz. The different frequencies are within a range of frequencies from about 1 MHz and about 3 MHz. The pulses have durations within a range of about 1 cycle to about 100 cycles. The different amplitudes compensate for different attenuation amounts associated with the different frequencies. The system includes a controller coupled to the transceiver and configured to actuate the transceiver to produce the mainbeam in a burst of multiple cycles, at least two of the cycles having at least one of different frequencies, different phases, and different amplitudes. The analyzing means is configured to provide an indication of whether the target region is at least partially fluid filled.

In general, in another aspect, the invention provides a system for delivering ultrasound signals to a target region in a subject using shear waves, the system including a transducer device configured to transmit and receive ultrasound energy, a controller coupled to the transducer device and configured to actuate the transducer device to transmit ultrasound energy toward the subject, and a positioning device coupled to the transducer device and configured to ensure that a portion of a first mainbeam from at least a portion of the transducer device is directed at a portion of a surface of the bone at an incident angle between normal incidence and a shear critical angle associated with the subject such that ultrasound energy in the first mainbeam will induce shear waves in the subject and energy from the first mainbeam will reach the target region, with energy in the shear waves forming a substantial part of energy of ultrasound waves at the target region, where the controller is configured to cause the transducer device to transmit energy in a at least one of: a single pulse including multiple cycles, at least two of the cycles having at least one of different frequencies, different phases, and different amplitudes, and a plurality of pulses, with different pulses having a different frequencies and amplitudes, and where the controller is configured to analyze ultrasound energy from the first mainbeam that is returned from the target region and is received by the transducer device to determine diagnostic information from the returned energy.

Implementations of the invention may include one or more of the following features. The transducer device comprises a plurality of elements configured to transmit ultrasound energy, and the controller is configured to inhibit actuation of at least one of (1) a portion of the transducer device configured to produce a second mainbeam that would be incident upon the portion of the surface of the subject at a second angle that is less than the longitudinal critical angle, and (2) a portion of the transducer device configured to produce a third mainbeam that would be incident upon the portion of the surface of the subject at a third angle that is greater than the shear wave critical angle. The different frequencies are within a range of frequencies from about 0.1 MHz and about 5 MHz. The different frequencies are within a range of frequencies from about 0.31 MHz and about 3 MHz. The pulses have durations within a range of about 1 cycle to about 100 cycles. The positioning device is configured to couple to the subject to mechanically orient the source relative to at least one of the subject and the bone as desired. The transducer comprises a plurality of elements configured to transmit ultrasound energy, and the positioning device is configured to affect phases of the elements to electronically steer the first mainbeam. The transducer comprises a plurality of elements configured to transmit ultrasound energy, and the controller is configured to affect timing of actuations of the elements to electronically steer the first mainbeam. The controller is configured to provide an indication of whether the target region is at least partially fluid filled based upon the diagnostic information determined by the controller from the returned energy.

Implementations of the invention may also include one or more of the following features. The controller is configured to cause a second mainbeam to be directed at the target region to stimulate motion in the target region, and w the controller is configured to provide an indication of the motion in the target region based upon the diagnostic information determined by the controller from the returned energy. The first and second mainbeams have different frequencies. The controller is configured to cause second and third mainbeams to be directed at the target region to stimulate motion in the target region, and the controller is configured to provide an indication of the motion in the target region based upon the diagnostic information determined by the controller from the returned energy. The controller is configured to produce an image of at least a portion of the target region from the returned energy. The target region is a linear region of the subject and the controller is configured to produce a linear image from the returned energy.

In general, in another aspect, the invention provides a method of delivering ultrasound signals using shear waves, the method including applying a portion of at least a first ultrasound beam to a subject at at least a first incident angle relative to the surface of the subject to induce shear waves in the subject, energy in the shear waves forming a substantial part of energy of first ultrasound waves at a desired region in the subject at a therapeutic level.

Implementations of the invention may include one or more of the following features. The portion of the first ultrasound mainbeam is applied to a surface of the subject between a longitudinal wave critical angle associated with the subject and a shear wave critical angle associated with the subject. Applying the portion of at least a first ultrasound beam comprises applying ultrasound energy at multiple incident angles between the longitudinal wave critical angle associated with the subject and the shear wave critical angle associated with the subject to focus ultrasound energy in the desired region. The method further includes applying at least a portion of a second ultrasound beam to the subject the subject to induce shear waves in the subject and to produce second ultrasound waves in the subject at the desired region, producing an image of at least a portion of the desired region, and identifying, from the image, whether ultrasound energy from the portion of the second ultrasound beam reaches the desired region in a desired manner. Applying the portion of at least a first ultrasound beam comprises applying the portion of at least a first ultrasound beam to bone. The bone is a skull, and the portion of the first ultrasound beam is directed at the skull at the at least a first incident angle in order to reach the desired region within the skull.

Implementations of the invention may include one or more of the following features. The portion of at least a first ultrasound beam is applied in multiple bursts of different frequencies. The different frequencies are within a range of frequencies from about 0.1 MHz and about 5 MHz. The different frequencies are within a range of frequencies from about 0.2 MHz and about 3 MHz. The pulses have durations within a range of about 1 cycle to continuous wave. Applying the portion of at least a first ultrasound beam comprises applying a portion of a third ultrasound beam to the subject to produce shear waves in the subject to produce third ultrasound shear waves in the desired region. The portion of the third ultrasound beam is separate from the portion of the first ultrasound beam. Applying the portion of at least a first ultrasound beam comprises applying a portion of a fourth ultrasound beam to the subject at a fourth incident angle that is less than the longitudinal wave critical angle associated with the subject.

In general, in another aspect, the invention provides a system for delivering ultrasound signals to a target region in a subject using shear waves, the system including a source configured to transmit ultrasound energy, and directing means, coupled to the source, for causing a portion at least a first mainbeam of the transmitted ultrasound energy to be incident upon a surface of the subject to induce shear waves in the subject, energy in the shear waves forming a substantial part of energy of first ultrasound waves at the target region in the subject at a therapeutic level.

Implementations of the invention may include one or more of the following features. The directing means is configured to direct the first mainbeam at the surface of the subject at a first angle between a longitudinal critical angle associated with the subject and a shear critical angle associated with the subject. The directing means comprises at least one of (1) a positioner configured to mechanically direct a normal direction associated with the source toward the surface at the first angle, and (2) a phase/delay adjuster, where the source comprises a plurality of radiating elements, the phase/delay adjuster being configured to regulate at least one of phases and delays of the plurality of radiating elements to electronically steer at least the first mainbeam. The positioner is configured to at least one of (1) couple to the subject and the source in a fixed manner such that the normal is directed toward the surface at the first angle, and (2) mechanically adjust the source such that the normal is directed toward the surface at the first angle. The source comprises a plurality of elements configured to radiate ultrasound energy, the system comprising a controller configured and coupled to cause at least a portion of the source to emit ultrasound energy, to process indicia of reflected energy due to the emitted energy to determine an orientation of at least a portion of the surface relative to the source, and to actuate only elements of the source that have their mainbeams at least partially directed at the portion of the surface between the longitudinal critical angle and the shear wave critical angle. The controller is configured to process the indicia of reflected energy to form an image of the at least a portion of the surface. The system includes a controller coupled to the source and configured to actuate the source to produce the first mainbeam and a second mainbeam at least a portion of which would be incident upon a surface of the subject at a second angle between the longitudinal critical angle associated with the subject and the shear critical angle associated with the subject such that ultrasound energy in the second mainbeam from the source will induce shear waves in the subject and energy from the second mainbeam will reach target region, where the second angle is different from the first angle.

Implementations of the invention may include one or more of the following features. The system includes a controller coupled to the source and configured to actuate the source to produce the first mainbeam for transmitting energy to the target region. The system includes a controller coupled to the source and configured to actuate the source to produce the first mainbeam in a plurality of pulses with different frequencies. The different frequencies are within a range of frequencies from about 0.1 MHz and about 5 MHz. The different frequencies are within a range of frequencies from about 0.2 MHz and about 3 MHz. The pulses have durations within a range of about 1 cycle to continuous wave. The system includes a controller coupled to the source and configured to actuate the source to produce the first mainbeam and a third mainbeam at least a portion of which would be incident upon a surface of the subject at a third angle that is less than the longitudinal critical angle associated with the subject.

In general, in another aspect, the invention provides a system for delivering ultrasound signals to a target region in a subject using shear waves, the system including a source configured to transmit ultrasound energy, a controller coupled to the source and configured to actuate the source to transmit ultrasound energy toward the subject, and a positioning device coupled to the source and configured to ensure that a portion of a first mainbeam from at least a portion of the source is directed at a portion of a surface of the subject at a first angle between a longitudinal critical angle associated with the subject and a shear critical angle associated with the subject such that ultrasound energy in the first mainbeam will induce shear waves in the subject and energy from the transmitted ultrasound will reach the target region, where the controller is configured to cause the source to transmit energy in a plurality of pulses, with each pulse having a different frequency.

Implementations of the invention may include one or more of the following features. The source comprises a plurality of elements configured to transmit ultrasound energy, and the controller is configured to inhibit actuation of at least one of (1) a portion of the source configured to produce a second mainbeam at least a portion of which would be incident upon the portion of the surface of the subject at a second angle that is less than the longitudinal critical angle, and (2) a portion of the source configured to produce a third mainbeam at least a portion of which would be incident upon the portion of the surface of the subject at a third angle that is greater than the shear wave critical angle. The different frequencies are within a range of frequencies from about 0.1 MHz and about 5 MHz. The different frequencies are within a range of frequencies from about 0.2 MHz and about 3 MHz. The pulses have durations within a range of about 1 cycle to continuous wave. The positioning device is configured to couple to the subject to mechanically orient the source relative to the subject as desired. The source comprises a plurality of elements configured to transmit ultrasound energy, and the positioning device is configured to affect phases of the elements to electronically steer the first mainbeam.

Various aspects of the invention may provide one or more of the following capabilities. Ultrasound can be propagated through bone, e.g., the skull, while experiencing reduced distortion and increased signal strength, allowing clearer and more accurate brain images, and better focusing for therapy applications compared to previous techniques. Unwanted echoes from overlying bone layers may be reduced, making analysis of diagnostic information received from target tissue easier. Bone cavities and/or their contents may be detected. Transbone shear mode propagation can be used for a number of imaging problems including vessel detection, tumor detection, tissue morphology, and hemorrhaging in the brain. Transbone ultrasound can be provided with reduced distortion and/or higher location accuracy than previous techniques.

These and other capabilities of the invention, along with the invention itself, will be more fully understood after a review of the following figures, detailed description, and claims.

DETAILED DESCRIPTION OF PREFERRED EMBODIMENTS

Figure 1:
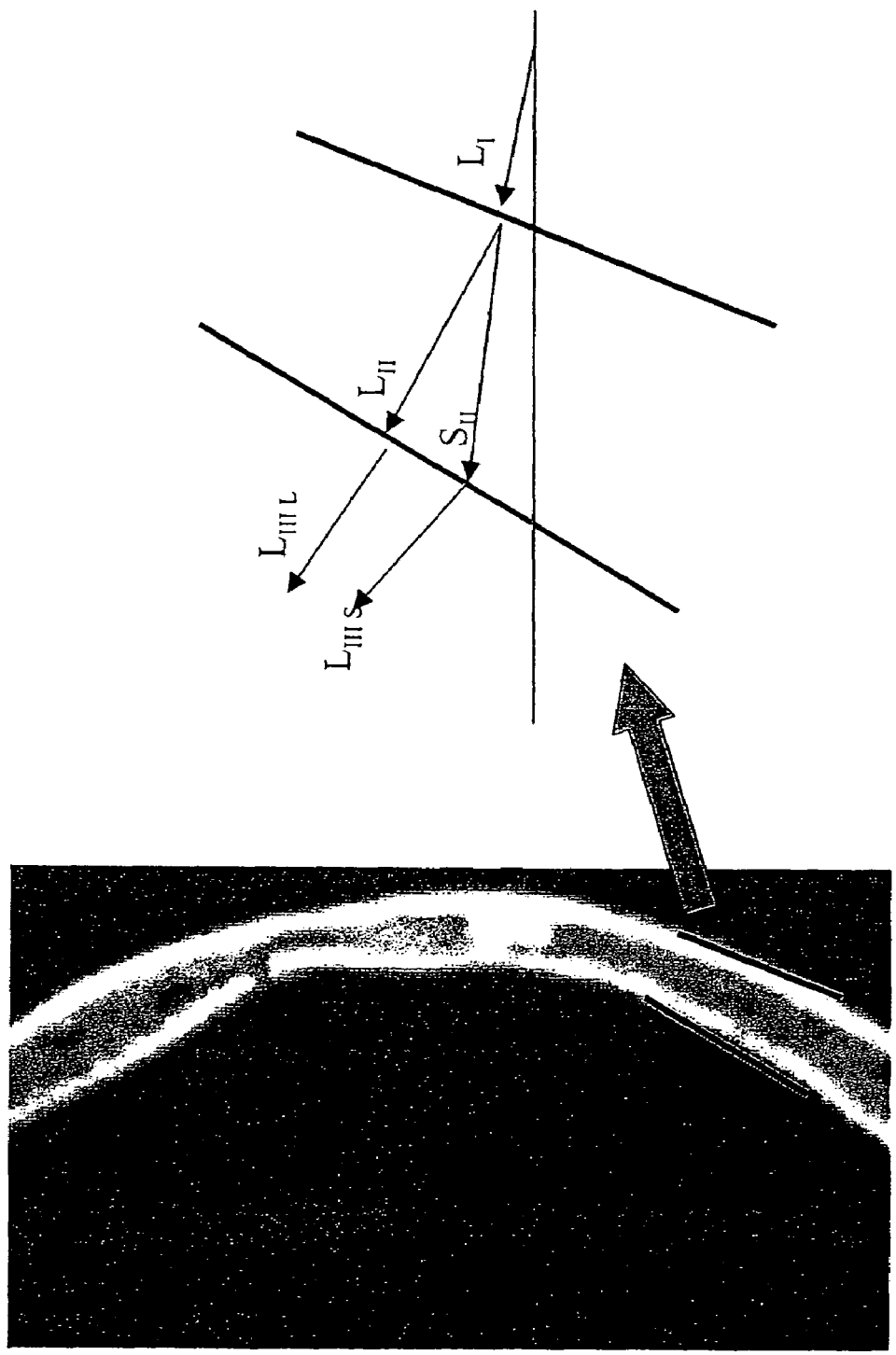
FIG. 1 is an image of a portion of a skull and a simplified line drawing of layers of the skull.

Embodiments of the invention provide techniques for transskull and other transbone propagation that deliberately induces a shear mode in bone. For transskull propagation, incident waves experience a mode conversion from an incident longitudinal wave into a shear wave in the bone layers and then back to a longitudinal wave in the brain. The skull's shear speed may provide a better acoustic impedance match, less refraction, and less phase alteration than its longitudinal counterpart. Using a shear wave, ultrasound may be focused in the brain. Longitudinal waves will not be induced in the bone if the ultrasound is incident upon the bone at an angle beyond Snell's critical angle. Numerical analysis is provided and demonstrations of the phenomena were studied with plastic phantoms and using an ex vivo human skull. Embodiments of the invention may be used for various applications, including therapeutic and diagnostic applications, which are discussed separately below. Other embodiments are within the scope of the invention.

It has been observed that under certain conditions it is possible to propagate ultrasound through the skull with reduced distortion and higher signal amplitudes by using high incident angles. Both numeric and experimental investigation indicate that this is due to the behavior of shear modes induced in the skull bone. When the ultrasound angle of entry is beyond Snell's critical angle for the longitudinal pressure wave, propagation in the bone is purely due to a shear wave. This conversion from a longitudinal wave (skin) to a shear wave (skull) and back to a longitudinal wave (brain) does not necessarily produce a highly distorted or small-amplitude wave. Investigations that studied isotropic phantom materials and later ex vivo human bone samples support this hypothesis. Indeed, it has been discovered that a focused beam, traveling as a shear wave in the skull, may be less distorted than a longitudinal one. In some instances a focused beam was observed to be larger in amplitude than a longitudinal wave propagated through the same skull area. The success of the longitudinal-shear-longitudinal propagation may be primarily due to the similarities between the elastic (shear) wave speed (~1400 m/s) and the sound speeds of water (~1500 m/s), skin (~1525 m/s), and the brain (~1550 m/s) and other soft tissues. In contrast, the range of longitudinal sound speeds in the skull at relevant frequencies is approximately twice these values. Thus, intentionally producing shear-modes in the skull bone may be used as a mechanism for producing brain images, or for detecting abnormalities within the brain. Similar techniques may be used for therapeutic and/or diagnostic uses in other parts of the body, or in applications aside from human or other animal bodies.

Embodiments of the invention use shear-modes intentionally produced in the skull bone as a mechanism for producing or enhancing a focus through the skull. Shear modes are incorporated into a transcrainal propagation model, demonstrating an ability to predict ultrasound phase and amplitude at high incident angles. To illustrate the approach, the field through a single plastic layer is first modeled. The approach is then applied to sections of human bone, which are compared to experimental measurements. The approach could be used for more accurate focusing in the brain and could extend the focusing region beyond current methods.

Theoretical Foundation

Based on the skull's small curvature relative to ultrasound wavelengths, the inner and outer surfaces of the skull are sectioned into regions that are each approximated as flat, but that are not necessarily parallel. This approximation is made to simplify the analysis and is not required for implementation of the invention. A diagram of the problem is given in FIG. 1, showing the ultrasound field divided into areas incident upon these regions of the skull surface. Each region is modeled as a single-layer isotropic solid with Lame constants determined as a function of the mean density over the propagation region.

Propagation through an arbitrarily oriented isotropic skull layer is achieved by spectral decomposition of the incident wave and determination of the ray paths, and attenuation as a function of angular wavenumber as the field crosses the skull. Each of these initially longitudinal harmonic spectral wave components will be considered below in terms of its velocity potential. Without loss of generality a given component may be viewed in a reference frame where the surface normal is oriented along Cartesian y-axis and the z-axis is defined by the unit vector of the cross product between the propagation axis and the surface vector. In this frame, the velocity potential is expressed as $$\phi^I = A_L^I e^{i(\omega t - k_x^I x \sin\theta^I - k_y^I y \cos\theta^I)} + A_{LR}^I e^{i(\omega t - k_x^I x \sin\theta^I + k_y^I y \cos\theta^I)}, \quad (1)$$

where $A_L$ is the amplitude of the longitudinal wave component incident upon the layer surface, $A_{LR}$ is the amplitude of the reflected longitudinal wave, $\theta$ is the angle of incidence and $k_x$ and $k_y$ are the wavevector components in the specified reference frame. The superscripts I to III are used to denote to the skin, skull and brain, respectively while the subscripts L and S refer to Longitudinal or Shear waves. Accordingly, the transmitted longitudinal potential in the skull is given by:

$$\phi^{II} = A_L^{II} e^{i(\omega t - k_x^{II} x \sin\theta^{II} - k_y^{II} y \cos\theta^{II})} \quad (2)$$

and the shear vector potential is $$\vec{\psi}^{II} = A_S^{II} e^{i(\omega t - k_{Sx}^{II} x \sin\theta_S^{II} - k_{Sy}^{II} y \cos\theta_S^{II})} \hat{z}. \quad (3)$$

Using this description, each spectral wave component must be viewed in its own unique reference frame. At the boundary, the incident wave is split into a reflected wave, a transmitted longitudinal wave and a transmitted shear wave. The amplitudes of these waves may be determined relative to the incident wave using methods outlined by Kino (*Acoustic Waves: Devices, Imaging, and Analog Signal Processing*, Englewood Cliffs, N.J.: Prentice-Hall, 1987). Specifically, the normal component of the particle displacement, $$\vec{r} = \nabla\phi + \nabla \times \vec{\psi} \qquad (4)$$

must be continuous at the boundary as well as the normal stress $$S_{yy} = \lambda \frac{\partial r_x}{\partial x} + (\lambda + 2\mu)\frac{\partial r_y}{\partial y} \qquad (5)$$

and the shear stress $$S_{xy} = \mu\left(\frac{\partial r_x}{\partial y} + \frac{\partial r_y}{\partial x}\right), \qquad (6)$$

with the shear and longitudinal sound speed of a given medium related to the Lamé constants $\mu$ and $\lambda$ by $$c_S = \sqrt{\frac{\mu}{\rho}},$$
$$c_L = \sqrt{\frac{\lambda + 2\mu}{\rho}}. \qquad (7)$$

Details of the amplitude calculations are provided in Appendix A. Each plane wave solution of describes the behavior of a single angular wavenumber. These amplitudes are calculated for each component wavevector space. However, this may be readily performed in closed form, as given in Appendix B.

After propagating into the skull, the longitudinal and shear waves are treated separately, with the total wave reaching the brain then equal to $$\phi^{III} = A_{LL}^{III} e^{i(\omega t - k_x^{III} x \sin\theta^{III} - k_y^{III} y \cos\theta^{III})} + A_{LS}^{III} e^{i(\omega t - k_x^{III} x \sin\theta_S^{III} - k_y^{III} y \cos\theta_S^{III})}, \qquad (8)$$

where $A_{LL}^{III}$ and $A_{LS}^{III}$ are the amplitudes of the longitudinal waves due to the incident longitudinal and shear waves in the skull.

The values of the velocity potentials may be found by equating Eqs (4)-(6) at the skin-bone interfaces after substituting in Eqs. (1)-(3), and solving for $A_L^{II}$ and $A_S^{II}$. At the skull-brain interface, the incident shear and longitudinal velocity potential amplitudes will be equal to the product of these transmission amplitudes and the absorption loss experienced within the bone. Since each spectral component will have its own independent path length through the skull, its total absorption will generally differ between components. A two dimensional representation of the problem is given in FIG. 1.

To find the wave amplitudes in the brain, $A_{LL}^{III}$ and $A_{LS}^{III}$, the problem is once again reduced to two dimensions by rotating the problem into a reference frame where the surface normal is oriented along Cartesian y-axis and the relevant wavevector lies in the x-y plane. Since the soft tissue of the brain is fluid-like, the incident longitudinal wave in the skull bone will be further divided into a reflected shear wave, a reflected longitudinal wave and a transmitted longitudinal wave. The shear wave in the skull will be similarly divided, but with differing reflection and transmission angles.

Figure 23:
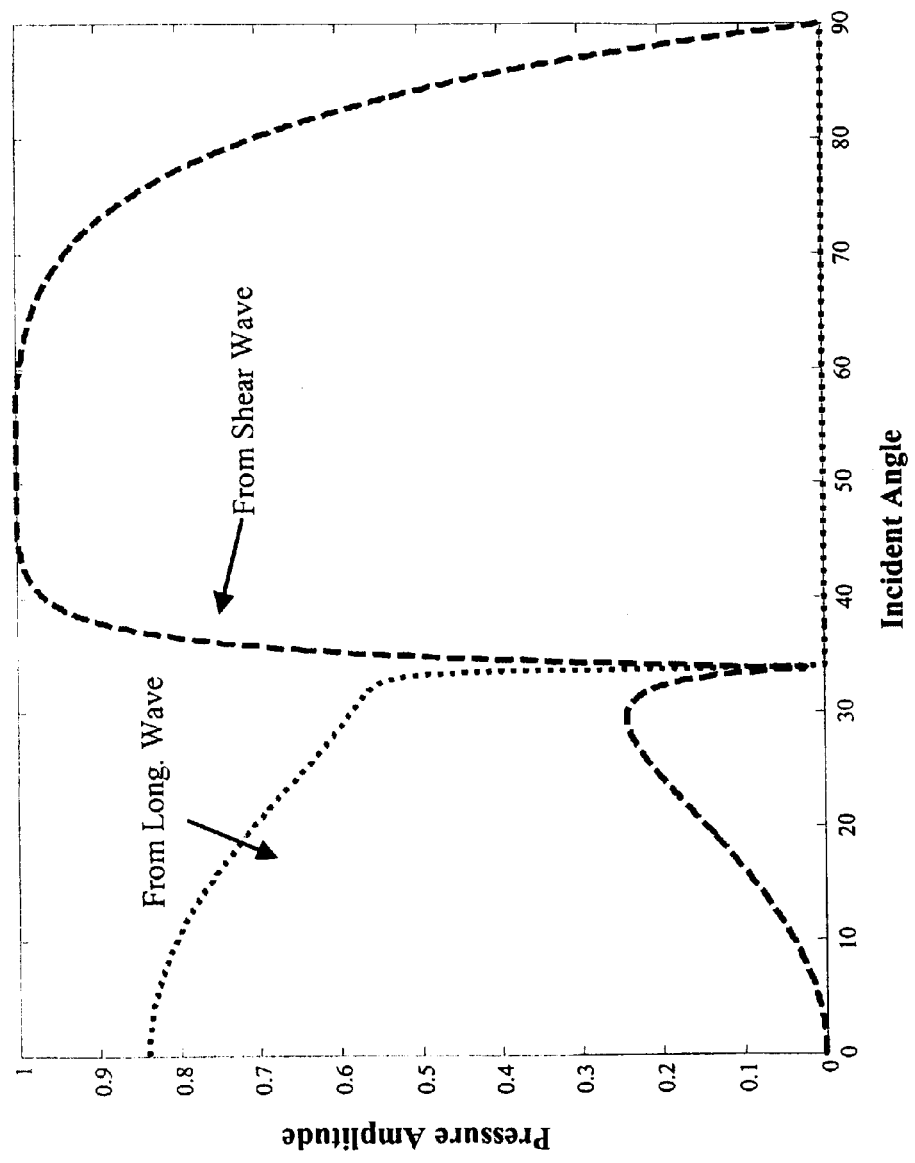
FIG. 23 is a graphical representation of pressure amplitude due to longitudinal and shear waves as functions of incident angle upon a plastic layer.

The acoustic pressure at a given point the brain is obtained by separately solving for amplitude and phase of each spectral component over a planar area. The spectrum is inverse-transformed to give the pressure over the measurement plane. The pressure amplitude is equal to the negative of the normal stress which is related to the amplitude of the scalar velocity potentials in the brain, $A_{LL}^{III}$ and $A_{LS}^{III}$ by Eq. (4) and Eq.(5). The pressure amplitudes were calculated as described in Appendix A. FIG. 23 shows the angular dependence of $A_{LL}^{III}$ and $A_{LS}^{III}$ resulting from an infinite plane wave in water after traveling through an ideal plastic (e.g., acrylic) layer.

Based on she skull's high attenuation coefficient, additional contributions due to multiple reflections within the skull bone are neglected. The total acoustic pressure at any point in the brain can be determined by calculating the path length and total transmission amplitude for each spectral component. The relative acoustic phase and the overall attenuation (including absorption loss) are calculated. The algorithm for determining the field path lengths from the transducer to the measurement point in the brain is presented in Appendix B.

Diagnostic Applications

Figure 2:
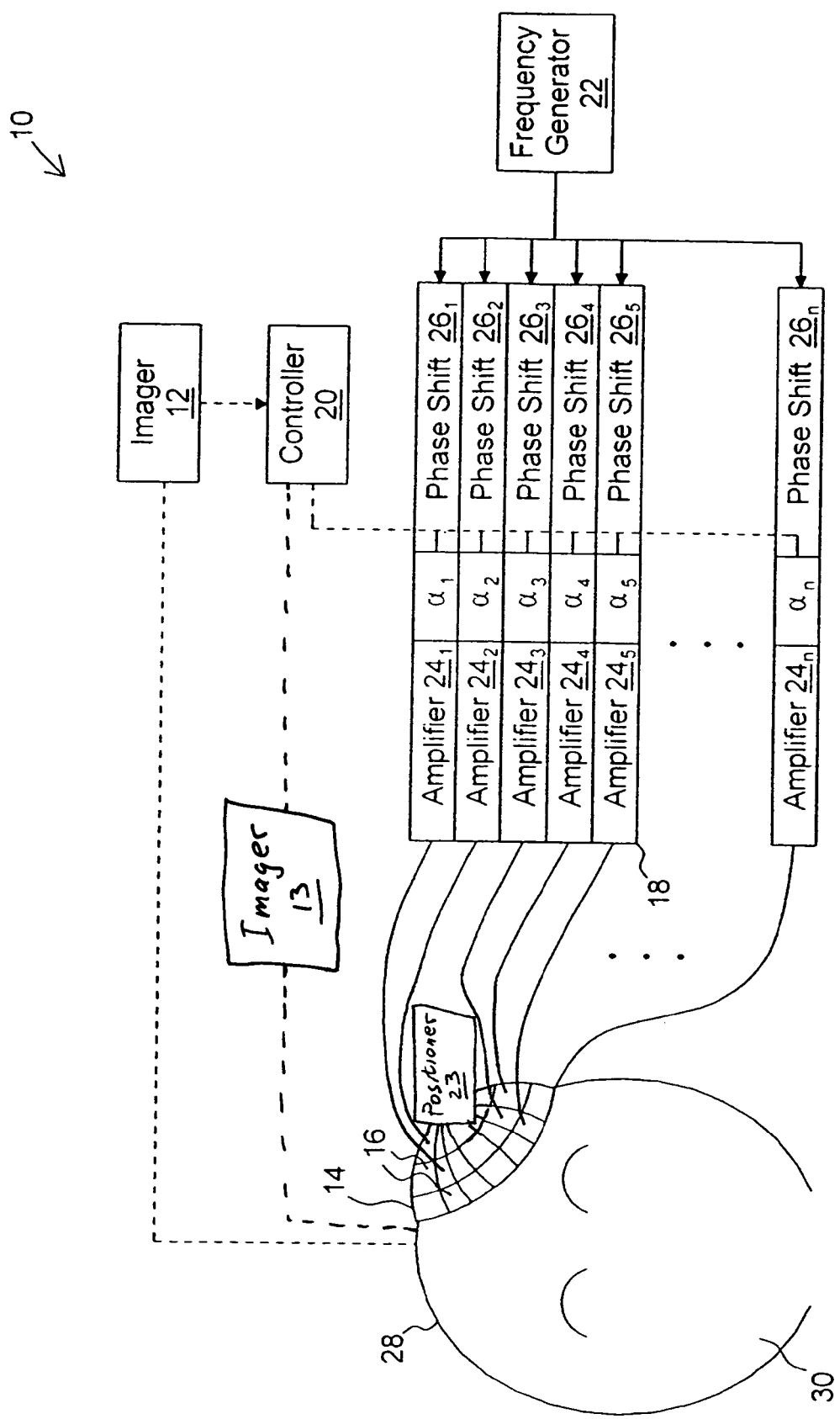
FIG. 2 is a schematic diagram of an ultrasound therapy system according to the invention.

Referring to FIG. 2, an ultrasound diagnostic system 10 includes an imager 12, a phased array 14 of n transducer elements 16, a signal adjuster 18, a controller 20, a frequency generator 22, and a positioner 23. The system 10 is configured to provide ultrasound diagnostic capabilities. The system 10 is configured to determine one or more characteristics of an object, here a skull 28 of a patient 30, and to apply ultrasound energy (e.g., in the range from about 0.01 MHz to about 10 MHz, and preferably between about 0.01 MHz and about 3 MHz) that is focused within the object, here in the patient's brain. While the discussion here focuses on a skull, other objects may be used, e.g., areas away from the brain, such as sinus cavities, ear canal, etc. Further, the invention may be used in dental applications (teeth), application through the ribs, spine, or any other bone. The invention could be used to determine if a cavity in a bone contains air or fluid and/or the viscosity of the fluid. In addition, the invention may be used to image bone marrow or nerves and vessels in the bones. Imaging of the spinal canal is also possible. The invention may also be used to detect bone cavities, fractures and/or tumors. The invention may also be used to determine properties of bone by comparing the shear wave speed and the longitudinal wave speed or by applying a force (e.g., an ultrasound-induced radiation force or a mechanical force) on the bone and using ultrasound to detect displacement.

Signals to the array 14 are provided by a driving arrangement. This arrangement may be similar to that reported in Daum et al., "Design and Evaluation of a Feedback Based Phased Array System for Ultrasound Surgery." IEEE Trans. Ultrason. Ferroelectr. Freq. Control 45(2):431-4, 1998, but with a driving frequency selected between about 0.1 MHz and about 10 MHz. The driving can be also performed by other techniques that provide desired ultrasound signals. The power and phase to each transducer element 16 may be manually controlled or automatically controlled using software and feedback. While an array of elements is preferred, the system 10 may be used with a non-coordinated set of elements, or even a single element, depending upon the application.

The array 14 of transducer elements 16 is configured to be disposed on or near the external surface of the patient's head or other surface overlying a bone 28. The array 14 is configured in a curved shape, e.g., spherical, although sections of other shapes are possible such as planar, including linear. The array 14 is configured to be placed on or near the patient's head and for focusing ultrasound energy at a distance from the surface of the array 14. The array 14 can be of a variety of sizes, e.g., 30 cm in diameter or larger to fit around a person's head, or about 1 mm in diameter or even smaller. The elements 16 are preferably transmitters configured to pulse, and direct, ultrasound at power levels that depend on the application, and in addition receive ultrasound energy. The transducer elements 16 of the array 14 are preferably piezoelectric transducer elements arranged in the array 14 as shown. The transducer elements 16 (e.g., piezoelectric ceramic pieces with a center-to-center spacing of $\lambda/2$) are mounted in silicone rubber or other material suitable for damping mechanical coupling between the elements 16. Other materials may also be used for the array construction. For example, the array 14 may be formed from one or more pieces of piezocomposite material, or any material that converts electrical energy to acoustic energy.

The array 14 is coupled to the signal adjuster 18 that is further coupled to the frequency generator 22. The frequency generator 22 is configured to provide a common radio frequency (RF) signal as the input signal to the signal adjuster 18. Also a separate signal generator could be used for some or all of the elements 16. The radio frequency generator 22 can be of any type that will produce the appropriate signals for the signal adjuster 18. Individual frequencies can also used. Using an individual signal generator (for example, digital waveform generators), the phase, amplitude, and delay of each signal can be set by the signal generators without an additional circuit. The excitations cause the ultrasound energy to transmit through the patient's skull 28 and, depending upon the relative delay, to focus the energy at a selected region within the patient's brain if desired. The generator 22 is coupled to the adjuster 18 to split the generator's output signal to provide n input signals to the signal adjuster 18.

Coupled to receive each of the n input signals from the frequency generator 22 are n pairs of amplifiers $24_1$-$24_n$ and associated delay circuits $26_1$-$26_n$ of the signal adjuster 18. Each pair of delay circuit 26 and amplifier 24 represents a channel of the signal adjuster 18. The delay circuits 26 are configured to provide n independent output signals to the amplifiers 24 by altering or adjusting the delay (and possibly amplitude) of the incoming signals from the generator 22 by respective delay factors $\alpha_1$-$\alpha_n$. The amplifiers $24_1$-$24_n$ are configured to amplify the signals from the delay circuits 26 and to provide the amplified signals to the transducer elements 16 through connections, e.g., coaxial cables, individually connecting the amplifiers 24 and the transducer elements 16.

The delay factors $\alpha_1$-$\alpha_n$ of the delay circuits 26 provide steering of the ultrasound beam absent an object in the path of the ultrasound energy. The phase delay for each element 16 associated with steering can be computed using known techniques. The delays $\alpha_1$-$\alpha_n$ are provided by the controller 20. The controller 20 includes logic that may be provided by software, hardware, firmware, hardwiring, or combinations of any of these. For example, the controller 20 can be a general purpose, or special purpose, digital data processor programmed with software instructions in a conventional manner in order to provide and apply the delays $\alpha_1$-$\alpha_n$ to the delay circuits 26, although other configurations may be used.

Figure 24:
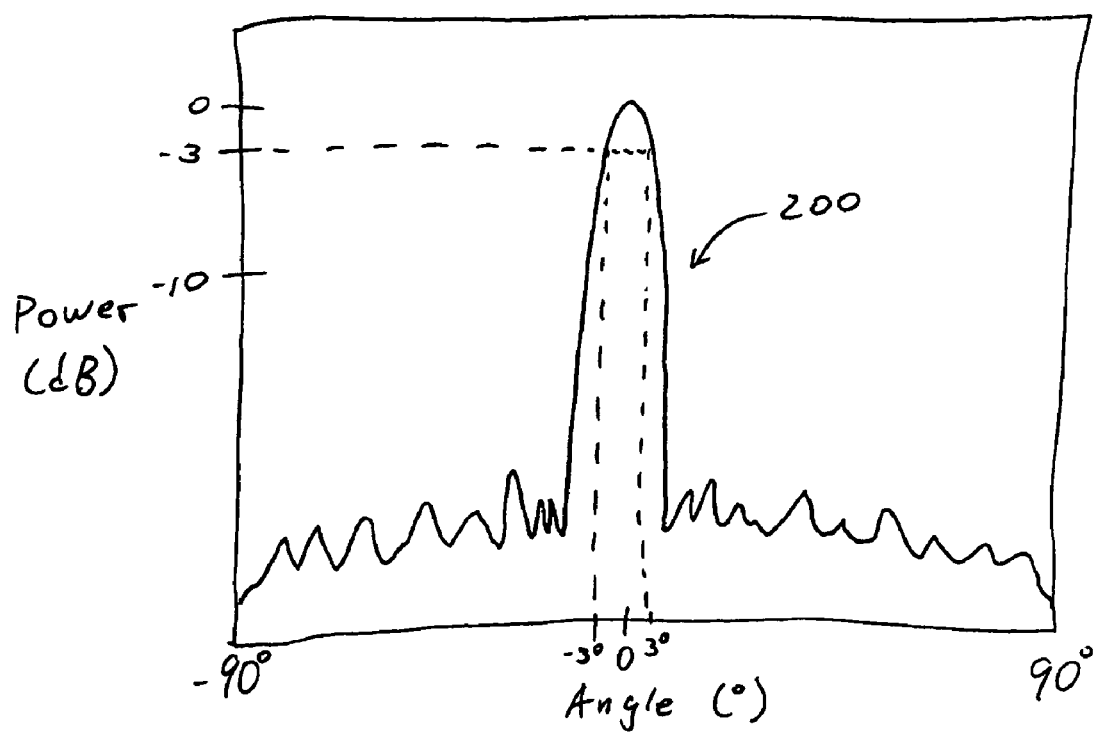
FIG. 24 is a graph of an exemplary, narrow mainbeam antenna pattern.
Figure 25:
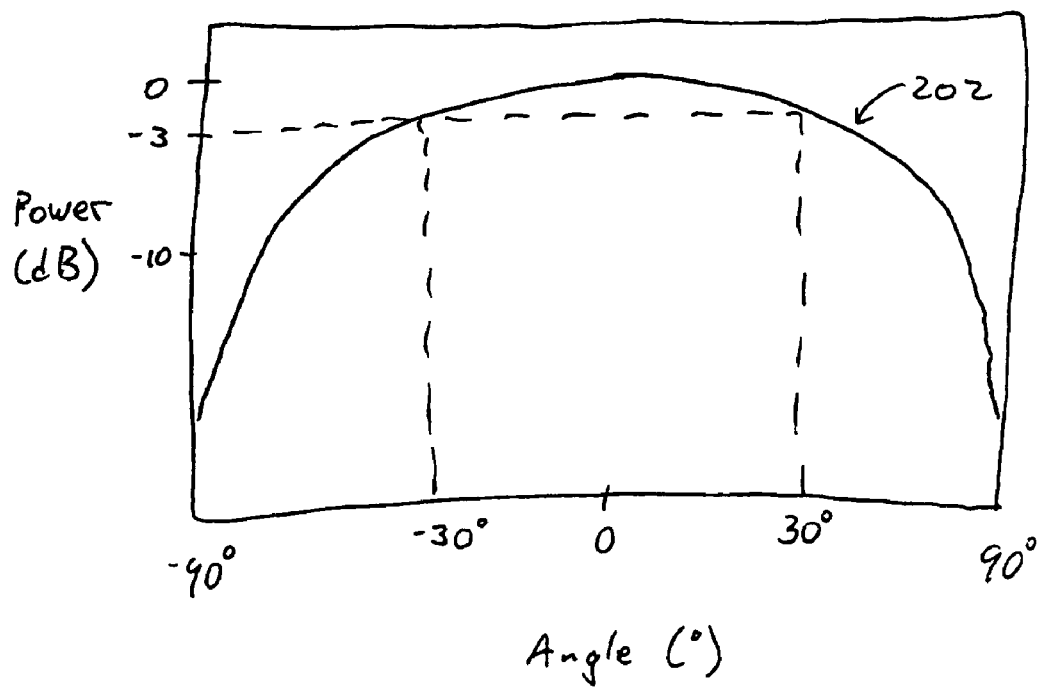
FIG. 25 is a graph of an exemplary, broad mainbeam antenna pattern.

The positioner 23 is configured to help ensure that the array 14 can provide ultrasound energy to the object 28 at angles to induce shear waves in the object 28. The positioner 23 may be shaped to orient the array 14 (or a single element 16) with respect to the outer surface of the object 28 such that a normal direction relative to the array 14, or single element 16, is between a longitudinal critical angle (Snell's angle) plus a lower safety factor and below the shear critical angle (above which shear waves will not be propagated into the object 28) minus an upper safety factor. For a soft tissue-skull interface, Snell's angle is about 20° and the shear critical angle is about 65° and thus ultrasound may be preferably directed at a skull between about 25° and about 60°. The safety factors may help account for a width of the mainbeam of the array 14 or element 16. Referring to FIGS. 24-25, a mainbeam 200 of the array 14 may be relatively narrow, e.g., ±3° at 3 dB down from the normal at 0°. A mainbeam 202 of a single element 16 may be much broader, e.g., ±30° at 3 dB down from the normal at 0°. For diagnostic applications, the mainbeam is preferably narrow whether it is from an array (large or small), or a single element. The positioner 23 helps to ensure that at least a desired portion of the mainbeam 200, 202 can be directed at the surface of the object 28 at an incident angle between the longitudinal and shear critical angles. For example, for a single element 16, the positioner 23 may be a block configured to receive the element 16 and to be placed on the surface of the object 28 to align the element 16 as desired. For example, the positioner 23 could be configured to be placed on a person's face adjacent the person's nose and to orient the element 16 such that at least a desired portion (e.g., with at least a threshold amount of power) of the mainbeam 202 will be directed into the skull of the person at an angle between the longitudinal and shear critical angles (e.g., toward the person's sinus cavity). Also, shallower angles between the critical angle for the longitudinal wave and the normal may be used.

The controller 20 is configured to direct ultrasound from the array 14 as desired. The controller 20 is configured to mechanically and/or electronically steer/direct ultrasound energy from the array 14. The controller 20 can send instruction signals to the positioner 23 to mechanically alter the position of the array 14 and thus the physical pointing of the array 14 (i.e., the direction of the mainbeam(s) from the array 14 and/or location(s) at which the mainbeam(s) is(are) incident upon the object 28). The controller 20 can further control the phase provided by the phase shifters 26, or the timing of excitations of the elements 16, to electronically scan the ultrasound beam from the array 14. Several techniques could be used for steering by controlling the excitation timing, e.g., the controller 20 could provide delayed excitation signals, or the controller 20 could provide a common excitation signal that is time delayed different amounts for different elements 16, etc. The controller 20 is configured to ensure that at least a desired amount of energy from the ultrasound mainbeam, be it mechanically and/or electrically steered, is directed into the object 28 between the longitudinal and shear critical angles. The ultrasound energy is converted from longitudinal waves into shear waves and transmitted in the object 28 as shear waves. Some energy, however, may be directed at the object 28 at angles above or below the range between longitudinal and shear critical angles. Further, the shear waves may be converted back to longitudinal waves in the object 28 if there is a transition in the object 28 (e.g., a change in acoustic impedance) that would induce such a conversion (e.g., a transition from skull to brain).

The mechanical direction/orientation of the array 14 may also be manually adjusted. Preferably, the angle of the surface of the object 28 is determined by sight, without the use of imaging equipment such as a CT (computer tomography) or MR (magnetic resonance) scanner. Guides, however, may be provided for indicating when a beam normal to the array 14 will produce a shear wave in the object 28. The controller 20 is further configured to selectively excite the elements 16. Thus, the controller 20 can selectively excite elements that will provide an incident angle to the object 28 that will produce a shear wave in the object 28 and not excite elements that will not produce a shear wave in the object 28. Further, multiple beams may be produced simultaneously from the array 14 directed at different locations, and of similar or different frequency and/or amplitude.

The controller 20 is configured to control the delay circuits 26 and the amplifiers 24, and to process data received from the object 28, here the skull 28, to provide diagnostic abilities. The controller 20 can cause the emitted ultrasound to be sent along a line within the object 28, and to be scanned (e.g., moved methodically) about a broader region of interest in the object 28. The line through the object 28 taken by the ultrasound may change directions (e.g., at interfaces of varying acoustic impedance). The controller 20 can process reflected energy received by the array 14 into an image based on the direction of the beam and the time between sending and receiving the energy. Also, the controller 20 does not have to process received energy to form an image of the object 28. The controller 20 can process the received energy to provide other diagnostic information, e.g., a binary indication of whether a void is detected (e.g., a cavity or abscess in a tooth or bone, such as a jaw bone), or the presence or absence of material in a void (e.g., fluid in a sinus cavity or inner ear), etc. The controller 20 can also process the information to form an image, e.g., of anatomy of the object 28, of blood perfusion in the object 28, etc.

The controller 20 is further configured to control the frequency generator 22, the amplifiers 24, and the delay circuits 26 to affect the frequency, magnitude, and phasing of ultrasound energy supplied by the array 14 to the object 28 for diagnostic applications. It has been discovered that a non-uniform excitation scheme helps overcome transmission attenuation, thus improving energy delivery and reception characteristics. The controller 20 is configured to cause the array to be excited with a series of extended bursts, thus producing a series of extended ultrasound bursts transmitted to the object 28. The bursts are preferably repeated over a range of frequencies and returned signals numerically combined. For example, 10 cycles of energy can be sent into the skull 28 at frequencies ranging from about 0.5 MHz to about 2.0 MHz at intervals of about 0.01 MHz. The amplifiers 24 are preferably controlled such that desired (e.g., uniform) signals are sent (or received) at each component in the spectrum. Also, power of the transmitted signals is preferably higher at higher, more attenuating frequencies (e.g., above about 1 MHz for skulls), for example being proportional to the two-way attenuation loss so that the received signal would have a more or less desired (e.g., equal) signal over the received frequency spectrum. The controller 20 is further configured to sum the received signals and to apply a matched filter to the signals to recover structural interfaces. The same can also be performed in a single transmitted ultrasound burst where the frequency is scanned over a desired range while modulating the amplitude in a desired manner to compensate for attenuation differences associated with the different frequencies. Frequencies between or within pulses can vary in virtually any manner, e.g., linearly increasing or decreasing, non-linearly increasing or decreasing, monotonically increasing or decreasing, randomly, etc. The controller 20 is further configured to control the delay circuits 26 to vary the phase between or within pulses. The controller 20 can cause the delay circuits 26 to cause different pulses to have different phases, and/or single pulses to have different phasing within the pulse.

Power levels for diagnostic applications vary depending upon the application. Typically, however, for diagnostic applications the burst duration is 1-100 cycles with a frequency between about 0.1 MHz and about 5 MHz, and preferably between about 0.5 MHz and about 3 MHz, although these values are exemplary only, and not limiting as to the scope of the invention.

The reflected signals received by the transducers 16 are converted to electric signals for processing by the imager 12. The imager 12 is configured to process the electric signals to form an image of the scanned region. The images can be provided to the controller 20, and may be obtained simultaneously with other uses of the array 14 (e.g., by intermittently applying energy for obtaining images, or by using some of the elements 16 for imaging and other elements 16 for other purposes).

The controller 20 is configured to analyze data from the array 14 and images from the imager 12. The controller 20 can process the reflected signals, analyzing the returned signals (or lack thereof) received by the elements 16 to identify indicia characteristic of a particular condition, e.g., fluid in a patient's sinus cavity.

Figure 3:
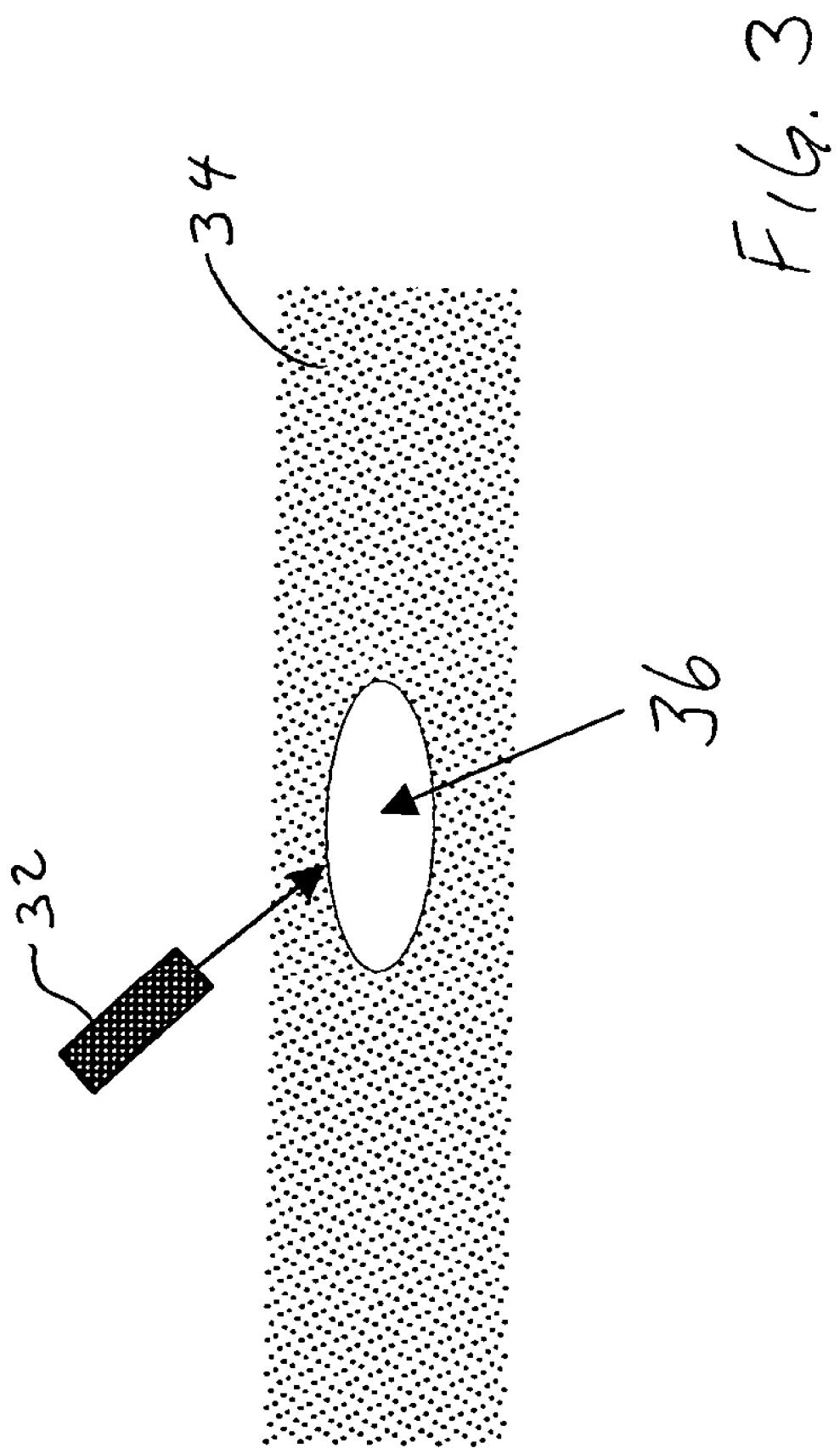
FIGS. 3-9 are schematic diagrams of exemplary portions of the system shown in FIG. 2 in use in various applications.
Figure 4:
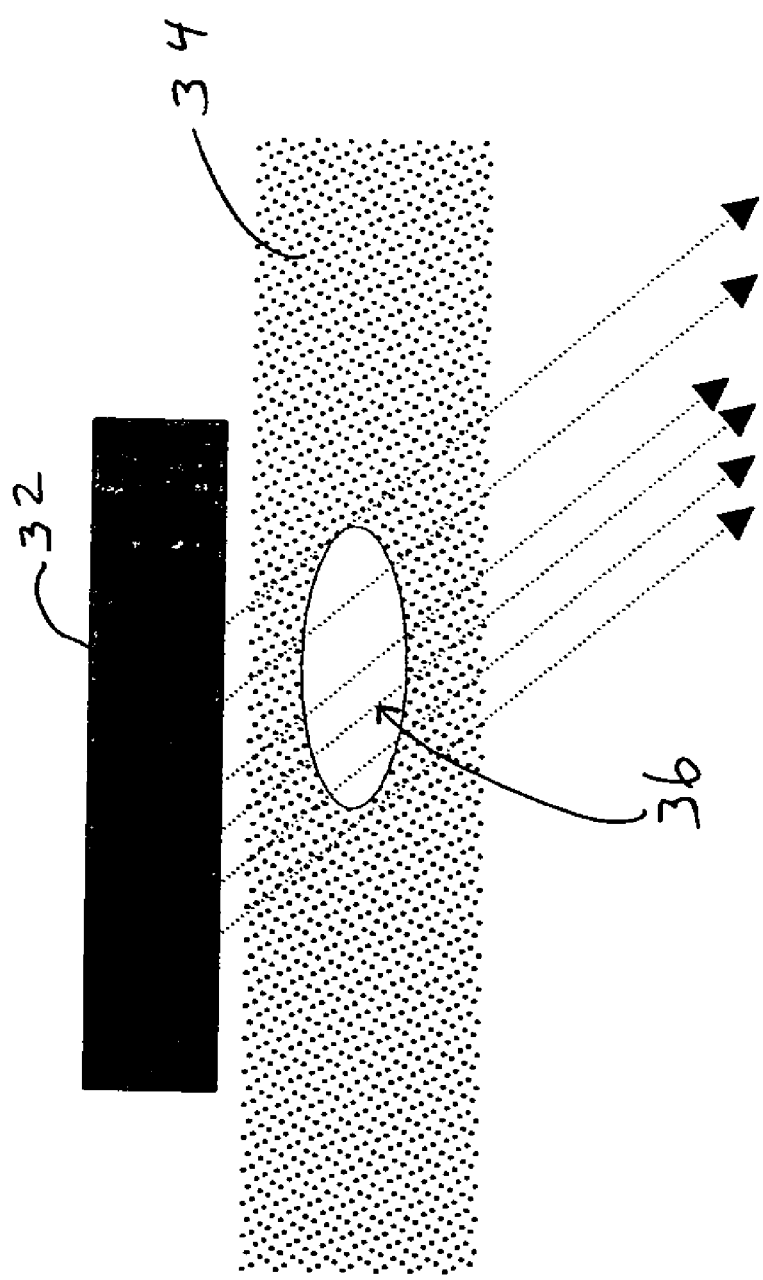
Figure 5:
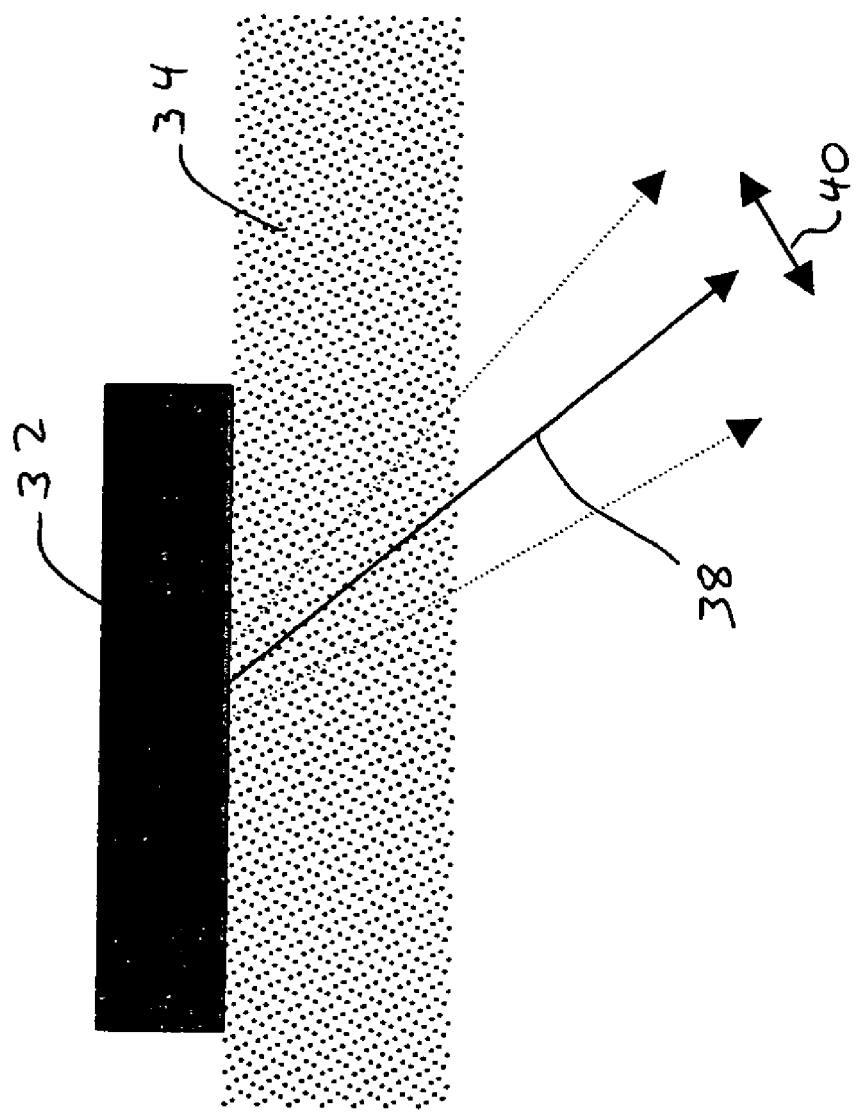

FIGS. 3-5, with reference to FIG. 2, show various configurations of the system 10, with only a portion of the system 10 shown, of particular use in diagnostic applications. For example, referring to FIGS. 3-4, a single transducer or a small array of transducers is used as an ultrasound transmitter 32 in lieu of the array 14. The configuration shown in FIG. 3 is preferably used for diagnostic applications where an image is not desired, while the configuration of FIG. 4 lends itself for use with or without producing images for analysis. For example, as shown, ultrasound shear waves may be directed through a material 34, such as a bone, in which there is a cavity 36 (such as a sinus cavity, or an abscess, etc.). Reflections may be analyzed by the controller 20 to determine various properties, such as whether the cavity 34 is fluid filled. FIG. 5 shows a configuration similar to that shown in FIG. 4, with electronic or mechanical scanning of transmitted shear waves 38 indicated by an arrow 40. While the shear waves 38 are shown unfocused, the phasing of elements in the transmitter 32 could be adapted to focus the waves 38.

Figure 8:
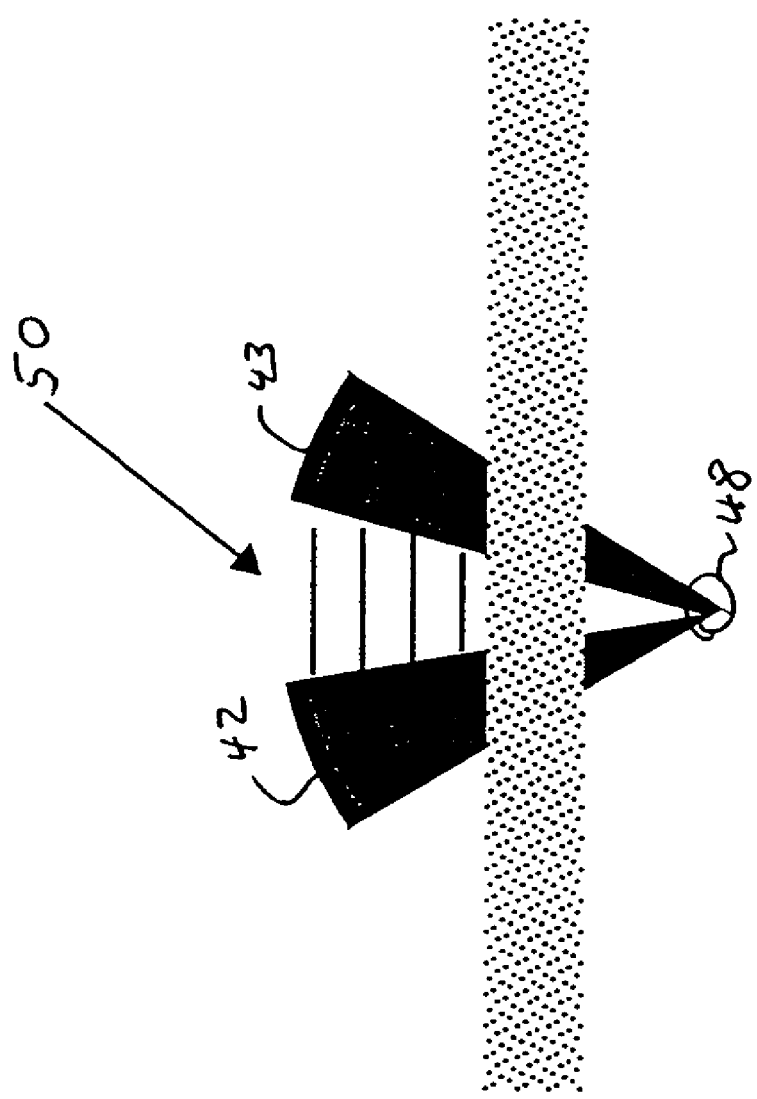
Figure 9:
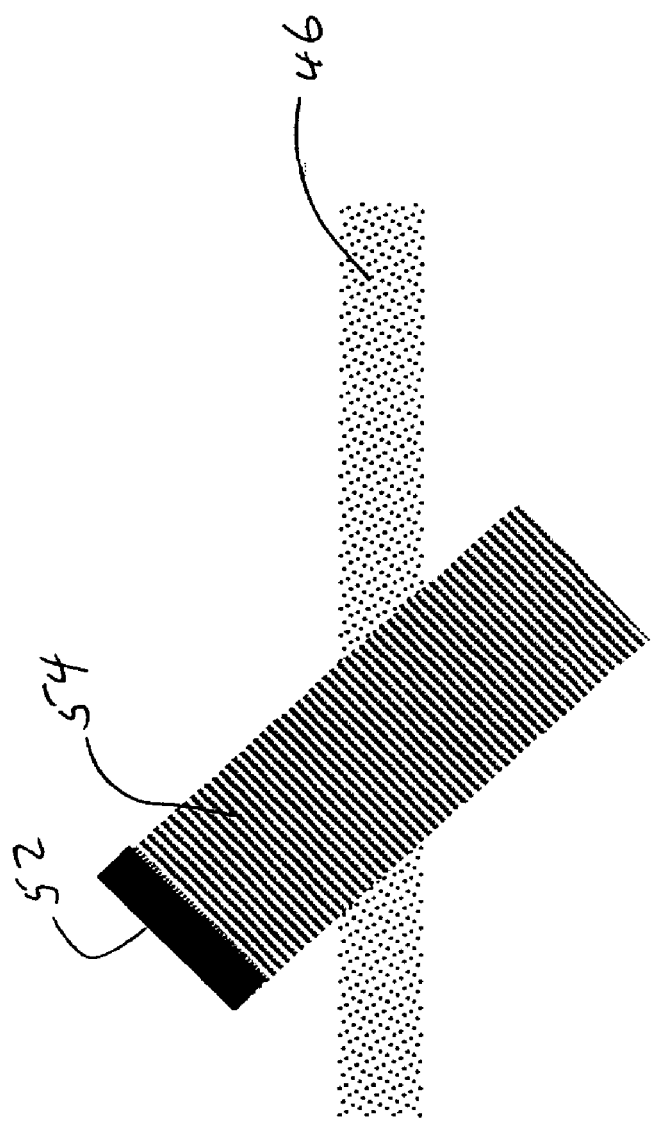
Figure 10:
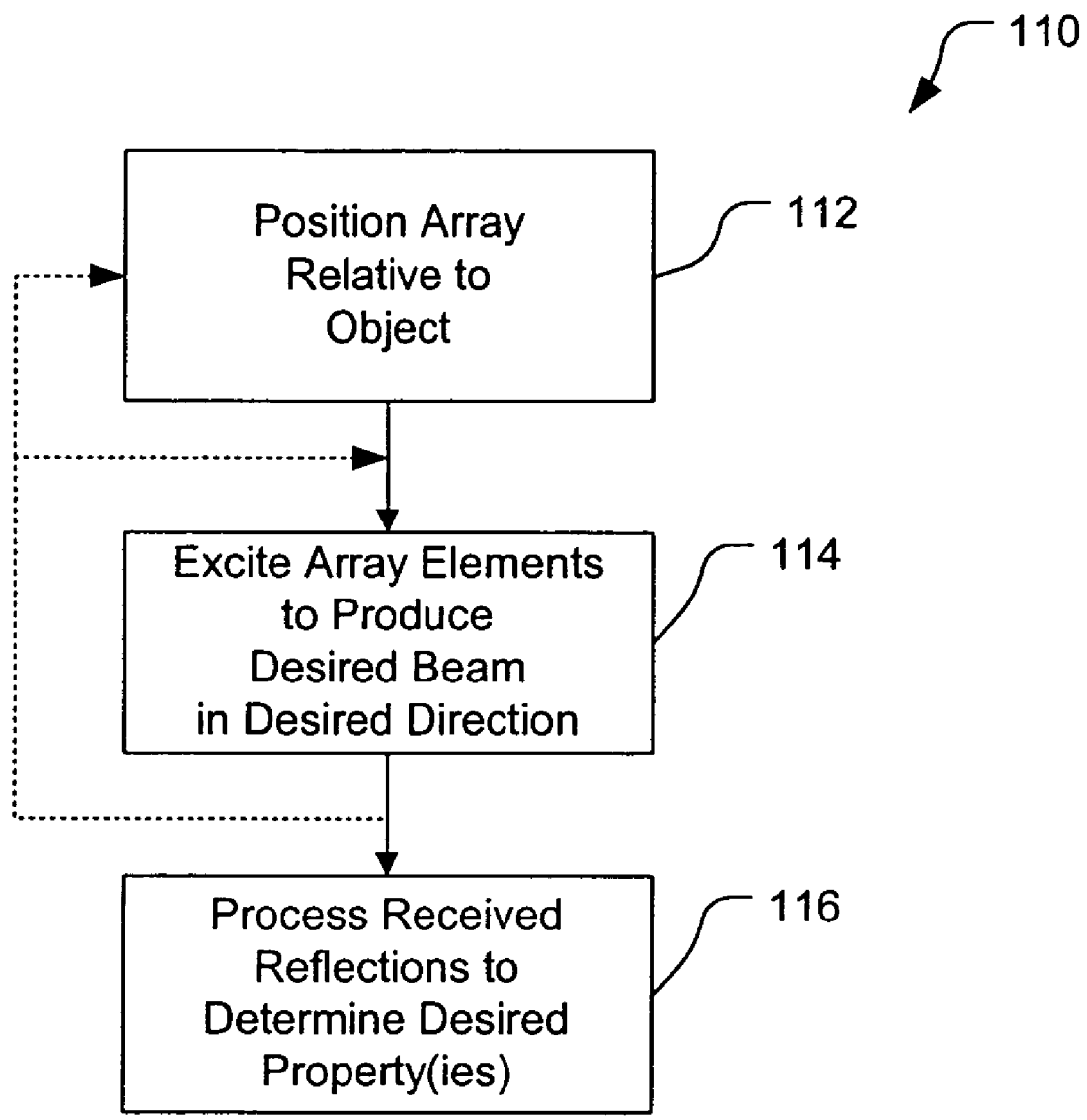
FIG. 10 is a block flow diagram of a process of using the system shown in FIG. 2 for ultrasound diagnostic applications.

In operation, referring to FIG. 10, with further reference to FIGS. 2-9, a process 110 for performing diagnostics on, and/or providing therapy to, an object using the system 10 includes the stages shown. For exemplary purposes, the object is assumed to be the skull 28 as shown in FIG. 2, although this is exemplary only and not limiting to the scope of the invention. The process 110, is exemplary only and not limiting, and may be altered, e.g., by having stages added, removed, or rearranged.

At stage 112, the array 14 is positioned relative to the object 28. The array 14 (or single element transceiver) may be positioned manually and/or by actuation of the positioner 23 by the controller 20. The array 14 is positioned such that it can transmit ultrasound energy to the surface of the object

28 to produce primarily shear waves in the object 28. The desired positioning may be determined in accordance with the angle of the surface of the object 28 as determined visually by an operator of the system 10. The angle of the surface of the object 28 may also be determined by actuating the array 14 and imaging the surface of the object 28. The image of the surface may be used to reposition the array 14 and/or to electronically steer the beam(s) from the array 14 as appropriate.

At stage 114, the transducer elements 16 are excited to produce a desired ultrasound beam directed at the object 28. The controller 20 selects the desired elements 16 for transmitting energy to provide the desired direction, coverage, and energy of the ultrasound energy to provide sufficient energy to a desired region or point to achieve desired results (e.g., for diagnosis, imaging, and/or therapy). The controller 20 regulates the frequency, phase, amplitude, and delay of the energy provided by the selected elements 16. The delay from element to element may vary to provide an electrically-controlled beam direction such that desired amounts of energy from the array 14 as a whole, and/or individual elements 16, are incident upon the object 28 at an incident angle between the longitudinal and shear critical angles, and are directed to reach a desired region in the object 28. The ultrasound energy is preferably provided in a coded manner as discussed above, with the energy being pulsed over a range of frequencies, with power magnitudes that vary in accordance with (depending on) the frequency of the signal transmitted. The beam may be broad or focused. Elements may also be selected and excited to provide ultrasound waves that will produce primarily longitudinal, not shear, waves in the object. The beam transmitted by the array 14 is incident upon the skull as longitudinal waves, passes through the skull as shear waves, and is converted back to longitudinal waves for further transmission (e.g., in the brain).

Stage 112 and/or 114 may be repeated depending upon the application. For example, for imaging, the array 14 may be repositioned mechanically and/or the direction of the ultrasound beam electronically steered to cover the entire area to be imaged.

At stage 116, for diagnostic or imaging applications, the imager 12 and controller 20 processes received reflections to determine appropriate characteristics. The imager 12 may process the received signals by collecting them in conjunction with the corresponding direction of the incident beam to produce an image of the object 28 (e.g., at a plane within the object 28). The controller 20 may manipulate the returned indicia to determine one or more properties not necessarily related to imaging, such as a determination that a cavity within the object 28 contains fluid or not. For diagnostic applications, the image(s) provided by the imager 12 may not be used by the controller 20, and indeed the imager 12 may not provide any images.

Therapeutic Applications

The system 10 may be used for therapeutic applications, in addition to or instead of diagnostic applications separately or simultaneously. The components of the system 10 generally operate as described above. For therapeutic applications, however, another imager 13 may be provided and the system 10 configured to provide ultrasound in a manner tailored for therapeutic use. The elements 16 are preferably configured to pulse, and direct, ultrasound with high power levels for therapeutic applications (the levels used depending upon the application).

The controller 20 is configured to control the phase shifters 26 and the amplifiers 24 for therapeutic applications. The controller 20 can cause the transmitted ultrasound to be focused on a focal region if appropriate for the therapy (e.g., thermal ablation) or to be applied to a broader region in an unfocused manner for appropriate therapy (e.g., low-power applications such as opening the BBB).

Power levels for therapeutic applications vary depending upon the application. Typically, for therapeutic applications, the burst duration is 1 cycle to continuous wave with a frequency between about 0.1 MHz and about 3 MHz, and preferably between about 0.2 MHz and about 2 MHz, although these values are exemplary only, and not limiting as to the scope of the invention. The sonications typically will include one burst or multiple bursts resulting in sonication times between about 1 microsecond and about 1 h or longer with varying times between pulses depending on the application.

The imager 13 can obtain images of the object 28 independently of the other apparatus of FIG. 2. For example, the imager 13 may be a computer tomography (CT) or magnetic resonance (MR) imager. The imager 13, like the imager 12, may provide images to the controller 20, e.g., for use in determining if adjustments are needed before or during therapeutic application of ultrasound using the array 14. The controller 20 is configured to determine from the images whether a desired region for receiving therapy is indeed receiving therapy, and receiving sufficient energy for the desired therapy. If a region other than the desired, target region is receiving the ultrasound energy (e.g., being ablated), or the desired region is receiving too much or too little energy, the controller 20 can alter the excitations of the elements 16 to correct the situation. For example, the energy can be increased or decreased, the focus of the energy made smaller or larger, the focal region can be changed or moved, etc.

Figure 6:
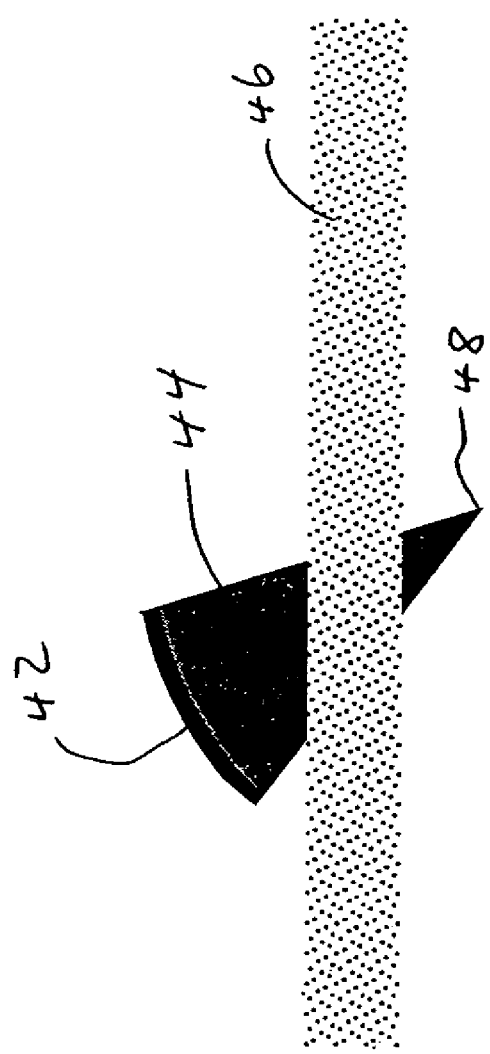
Figure 7:
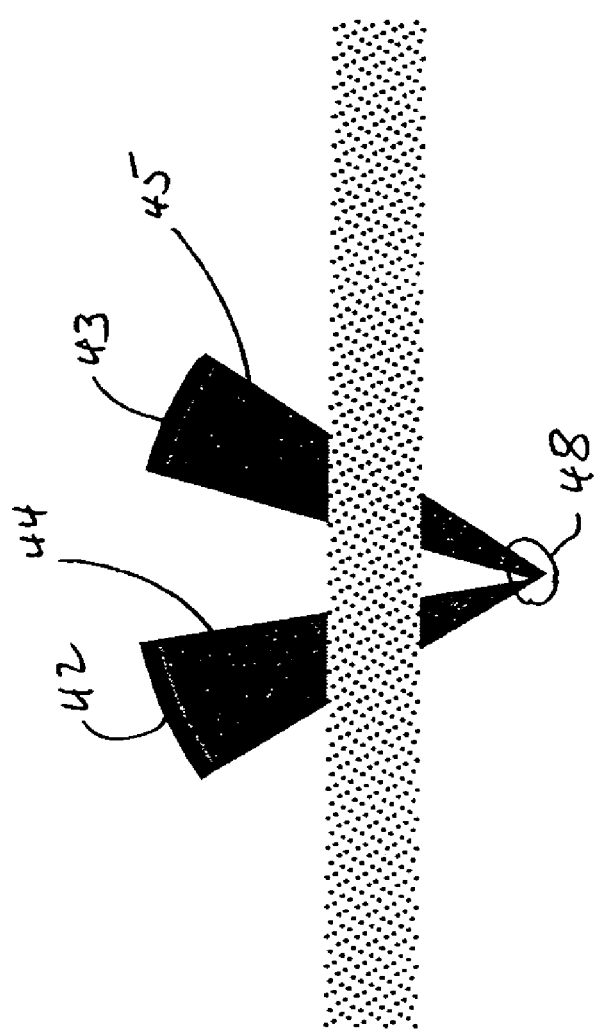

FIGS. 6-9 show various configurations adapted for use in therapeutic applications such as thermal ablation, mechanical destruction of tissue or tumors, BBB opening, gene therapy, targeted drug therapy, acceleration of chemical reactions, aiding for diffusion of chemicals, hyperthermia, applications increasing temperature of a region, any other ultrasound interaction that has therapeutic value, etc. FIG. 6 shows a single, curved transmitter 42, that may be a single element, or an array of elements. The transmitter 42 is configured to produce a focused ultrasound beam 44 that is transmitted through an object 46 (e.g., a skull) as shear waves, and that is focused at a focal point or region 48. Note that the ultrasound beam 44, as beams in other configurations discussed, is made of longitudinal waves between the transmitter 42 and the object 46 and shear waves in the object 46. If the makeup of the object 46 changes (e.g., from bone to a cavity, be it filled or not, e.g., with fluid or other matter such as brain tissue), the transmitted beam may return to longitudinal waves. This is the case when the object 46 is a skull. FIG. 7 illustrates a configuration similar to that of FIG. 6, but with two transmitters 42, 43 configured to focus their respective beams 44, 45 on the focal point/region 48. The transmitters 42, 43 may be different portions of a single array, or physically different, e.g., different arrays, different single elements, or a single element and an array. FIG. 8 illustrates a configuration similar to FIG. 7, but with incident ultrasound waves 50 also used that produce longitudinal waves in the object 28. This configuration may be used, e.g., when power is desired in addition to the power that the transmitters 42, 43 can provide. The longitudinal waves may be provided by the array 14, which the transmitters 42, 43 may be part of as well. FIG. 9 illustrates the use of a linear transmitter 52 (e.g., a single element or an array of elements) displaced from the object 46 and transmitting non-focused ultrasound energy of a sufficient level for a therapeutic application (e.g., opening the BBB, release or activation of chemicals or genes or other materials, etc.). As shown, the transmitter is mechanically positioned to provide a beam 54 that is normal to the transmitter 52 and between the longitudinal and shear critical angles with respect to the object 46.

Figure 26:
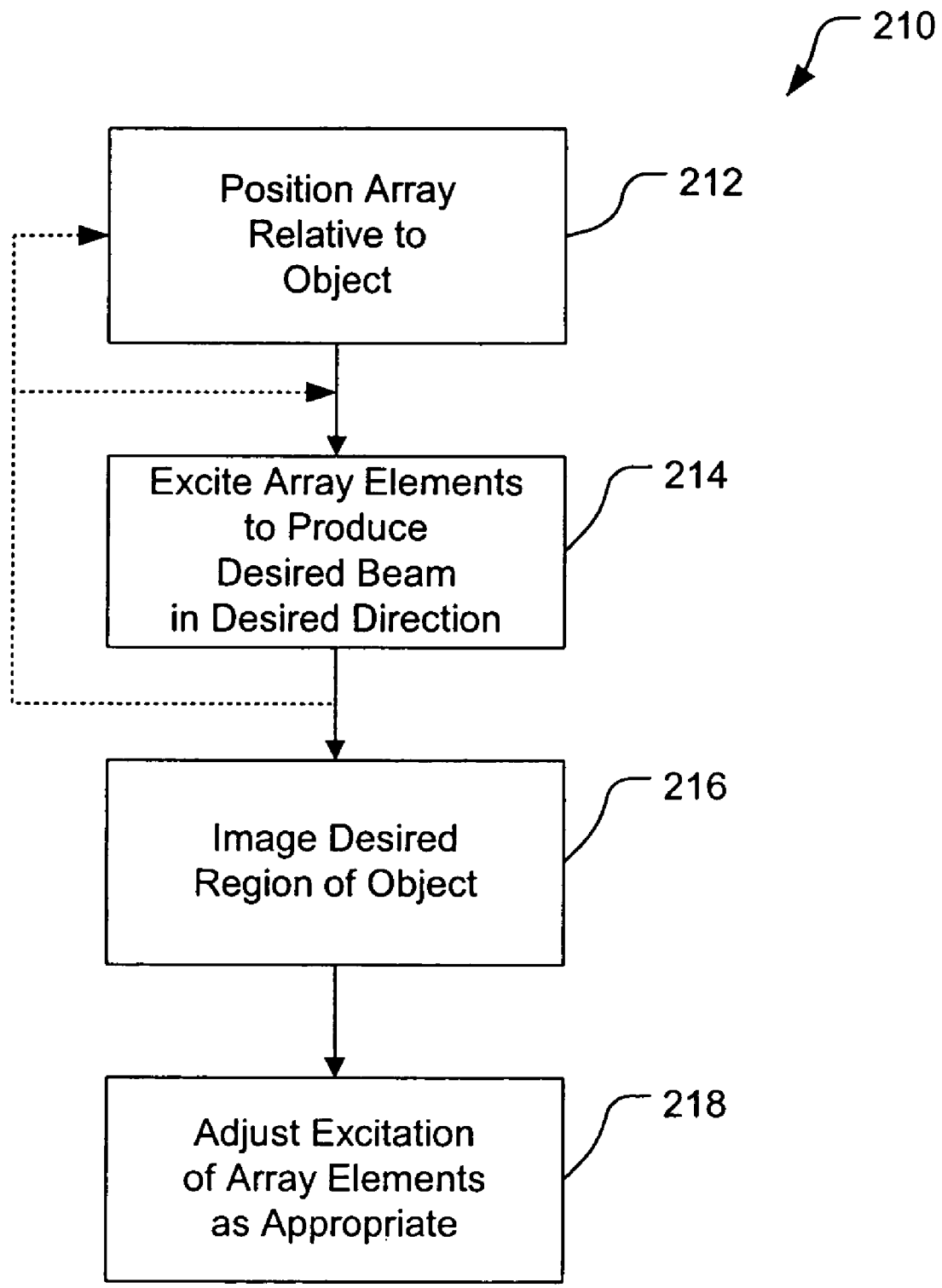
FIG. 26 is a block flow diagram of a process of using the system shown in FIG. 2 for ultrasound therapeutic applications.

In operation, referring to FIG. 26, with further reference to FIGS. 2-9, a process 110 for providing therapy to an object using the system 10 includes the stages shown. For exemplary purposes, the object is assumed to be the skull 28 as shown in FIG. 2, although this is exemplary only and not limiting to the scope of the invention. The process 210, is exemplary only and not limiting, and may be altered, e.g., by having stages added, removed, or rearranged. Stages 212 and 214 are similar to those discussed above.

At stage 216, the desired region of the object 28 is imaged. The imager 12 and/or 13 is(are) used to image the desired region, and preferably the surrounding volume such that the focus accuracy of the applied ultrasound can be evaluated.

At stage 218, appropriate corrections are made to the incident ultrasound energy for therapeutic applications. If images produced by the imager 13 (or by the imager 12 if the array 14 is suitable to both image and provide therapy) indicate that the applied ultrasound energy should be adjusted, then the controller 20 acts accordingly. The images may be analyzed, e.g., to see if a desired region, and only the desired region, is being heated and determining what, if anything, is less than desirable about the applied ultrasound. For example, the ultrasound energy may be focused poorly, or in the wrong spot, or too narrowly, or of too low or too great of power, etc. The controller 20 can cause the beam to be modified by adjusting the phase, amplitude, delay, and or frequency of excitation in accordance with the analyzed images to adjust/correct the applied energy to yield a desired focus and amount of energy in the object 28 at the desired location. The controller 20 can also cause the positioner 23 to alter the orientation and relationship of the array 14 relative to the object 28 as desired. Adjustments are preferably made before application of full power for therapy (e.g., thermal ablation or other non-reversible procedures). For example, less than full power may be applied, a preliminary determination made from the images made as to whether and what adjustments should be made, adjustments made, and then full therapeutic power applied by the array 14. Adjustments may also be made during application of full therapeutic power based on progress of the therapy.

EXPERIMENTS AND EXPERIMENTAL RESULTS

A parallel plastic plate phantom was used to test the algorithm in order to provided an idealized isotropic case that could readily be verified by experiment. Relevant values for the plastic are summarized in Table I. The ultrasound source was a 1.5 MHz focused transducer with a diameter of 12 cm and a radius of curvature equal to 16 cm. The source function for the algorithm was acquired by projecting a laboratory-measured pressure field from a plane near the geometric focus backward to the source. This field was measured over a 30×30 area with a spatial resolution of 0.5 mm. The source function was propagated through the plates using an algorithm described numerically in Appendices A and B. The distance from the source to the measured plane was 121 mm and the distance from the plastic inner surface to the source was 61 mm.

Similar methodology was used to propagate through ex vivo human calvaria (brain cages). Following the laboratory measurements, water was used as the interfacing medium with the inner and outer skull surface. The ultrasound source for the transskull measurement was a 0.74 MHz focused transducer with a diameter of 8 cm and a radius of curvature equal to 15 cm.

The numeric algorithm is implemented in Matlab®, using matrix-based operations for the layers. Operations were performed on a 1 GHz AMD-Based PC. A typical projection of a complex 128×128 matrix through five layers took approximately 30 s to calculate.

TABLE I

| Material | Density (kg/m$^3$) | Abs L | Abs S | $C_L$ (m/s) | $C_S$ (m/s) | Thickness (×10$^{-3}$ m) |
|---|---|---|---|---|---|---|
| Plastic 1 | 1187 | 45 | 50 | 2185 | 1330 | 11.8 |
| Skull 0 | NA | | | | | |
| Skull 1 | 2186 | 85 | 90 | 2850 | 1400 | 5.29 |
| Water | 1000 | 0 | 0 | 1486 | NA | Variable |

Laboratory Measurements

Skull Registration and Density

Data for the simulation was obtained from a digitized human head profile obtained using CT images (Siemens, SOMATOM, AH82 Bone Kernel). Both the coordinates of the skull surfaces as well as the internal density variation are obtained from these images. Scans were taken at 1 mm intervals using a 200 mm×200 mm field of view. A polycarbonate stereotaxic frame was attached around each sample to allow the skulls to be attached to the array and provide a reference for the mechanical positioning system and the CT images. The calculation was performed only in bone lying within the beamwidth of the section being considered. Information about the shape and structure of an individual calvarium was obtained from combining the images, that returned intensities proportional to material density.

Coordinates of points along the inner and outer surfaces of the skull were identified on an image using a threshold filter that searched for the innermost and outermost densities >1.4 gm/cm$^3$ along each line of an image. Points of successive images were combined to give three-dimensional representation of the inner and outer skull surface. Pixel intensities of each image were also combined into a three-dimensional array for later processing.

The phasing algorithm relied on precise knowledge of the orientation of the skull relative to individual array elements. To achieve this task in practice, the phasing algorithm translated and rotated the skull data from the CT coordinate frame to the transducer coordinate frame as well as translated and rotated the skull from the mechanical positioning system's coordinate frame to the transducer coordinate frame. The program operated using three markers located on the polycarbonate frame affixed to the skull. These locations could be identified mechanically with the positioning system to a precision of approximately 0.1 mm. The algorithm generated a rotation matrix that mapped between the coordinate systems.

Ultrasound Measurements

Propagation experiments were set up in a water tank to verify the numeric algorithm. Measurements were performed in degassed and deionized water in a tank padded with rubber to inhibit reflections. Ultrasound signals were generated by a transducer specific to the particular measurement and received with a Polyvinylidene difluoride (PVDF) needle hydrophone (Precision Acoustics, Dorchester, UK). To help assure a strong reception while maintaining accuracy, a 0.2 mm-diameter hydrophone was used for 1.5 MHz measurements and a 0.5 mm-diameter hydrophone was used for measurements at 0.74. MHz. The smaller hydrophone at higher frequency was used to help minimize hydrophone directivity and to help prevent phase averaging. A skull (or plastic plate) was placed between the hydrophone and transducer at an angle controlled by a rotational stepping motor (made by Velmex of Bloomfield, N.Y.). A 3D linear positioning system (Velmex, Bloomfied, Model V P9000) allowed the hydrophone to be scanned over a measurement area centered about the transducer's axis of symmetry. Transducer signals were generated by an arbitrary waveform generator (made by Wavetek, of Norwich, UK, Model 305) fed to a power amplifier (made by ENI, of Rochester, N.Y., Model 2100L). The hydrophone's voltage response was sent though a Precision Acoustics pre-amp and an amplifier (made by Preamble Instruments, of Beaverton, Oregon, Model 1820) before it was recorded by a digital oscilloscope (made by Textronix, of Wilsonville, Oreg., Model 380). The voltage waveform was downloaded to a PC by GPIB (General Purpose Interface Bus) control and the amplitude and phase at the measurement location were calculated from the FFT of the signal, taking values at the transducer driving frequency.

The 11.8 mm plastic plate was placed in the test tank and the acoustic transmission was measured on the transducer's axis of symmetry, 121 mm from its face. The acoustic pressure was measured between −70° and 70° at an increment of 1°. Agreement between the measured and simulated waveforms was evaluated by comparing the amplitudes and phases at each angular orientation. The source function for the simulation was a pressure field measurement taken with the transducer in water without a plate present.

Figure 11:
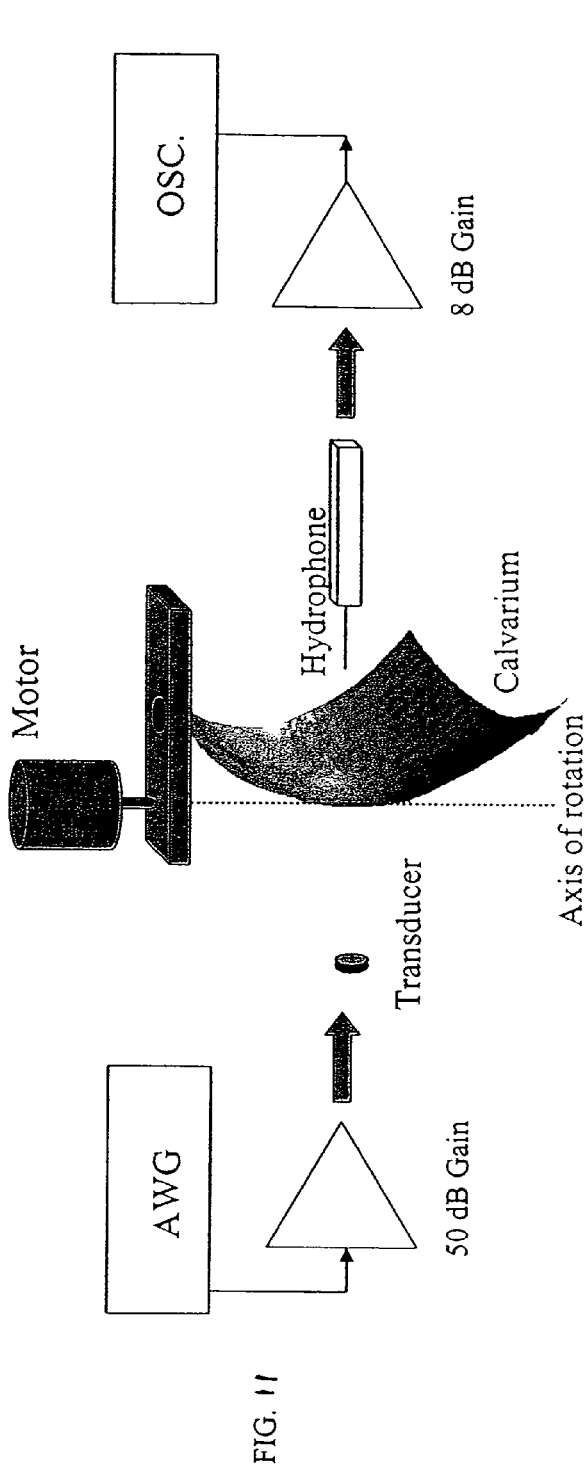
FIGS. 11-12 are two different mounting procedures used in experiments for transskull measurements.
Figure 12:
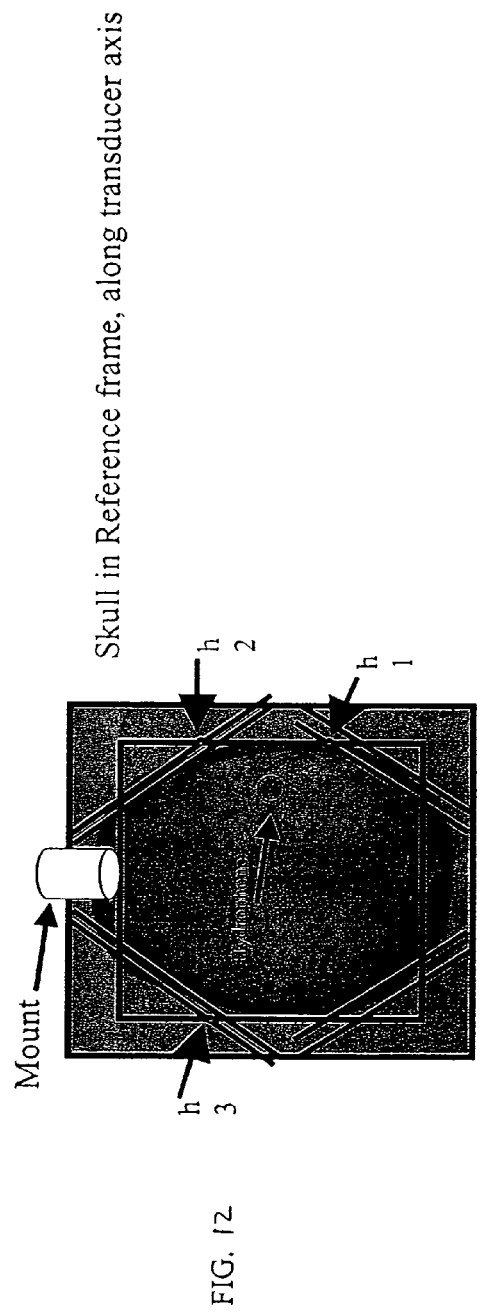

For the transskull measurements, two different mounting procedures were performed. The first, shown in FIG. 11 was designed to allow measurement through an approximately constant location on the skull at different incident angles. The second configuration, shown in FIG. 12, allowed measurement at high incident angles with good registration between the transducer and the skull, but did not facilitate movement of the skull. Initial measurements examined the angular dependence of amplitude on the skull, in order to determine whether amplitude peaks were present beyond the longitudinal Snell's critical angle. A section of skull bone skull was rotated between 0° and 55°, with the axis of rotation normal to the transducer axis and coincident with a line through the bone. The maximum angle of 55° was the highest value obtainable with the setup.

Results

Plastic Phantom

Figure 13:
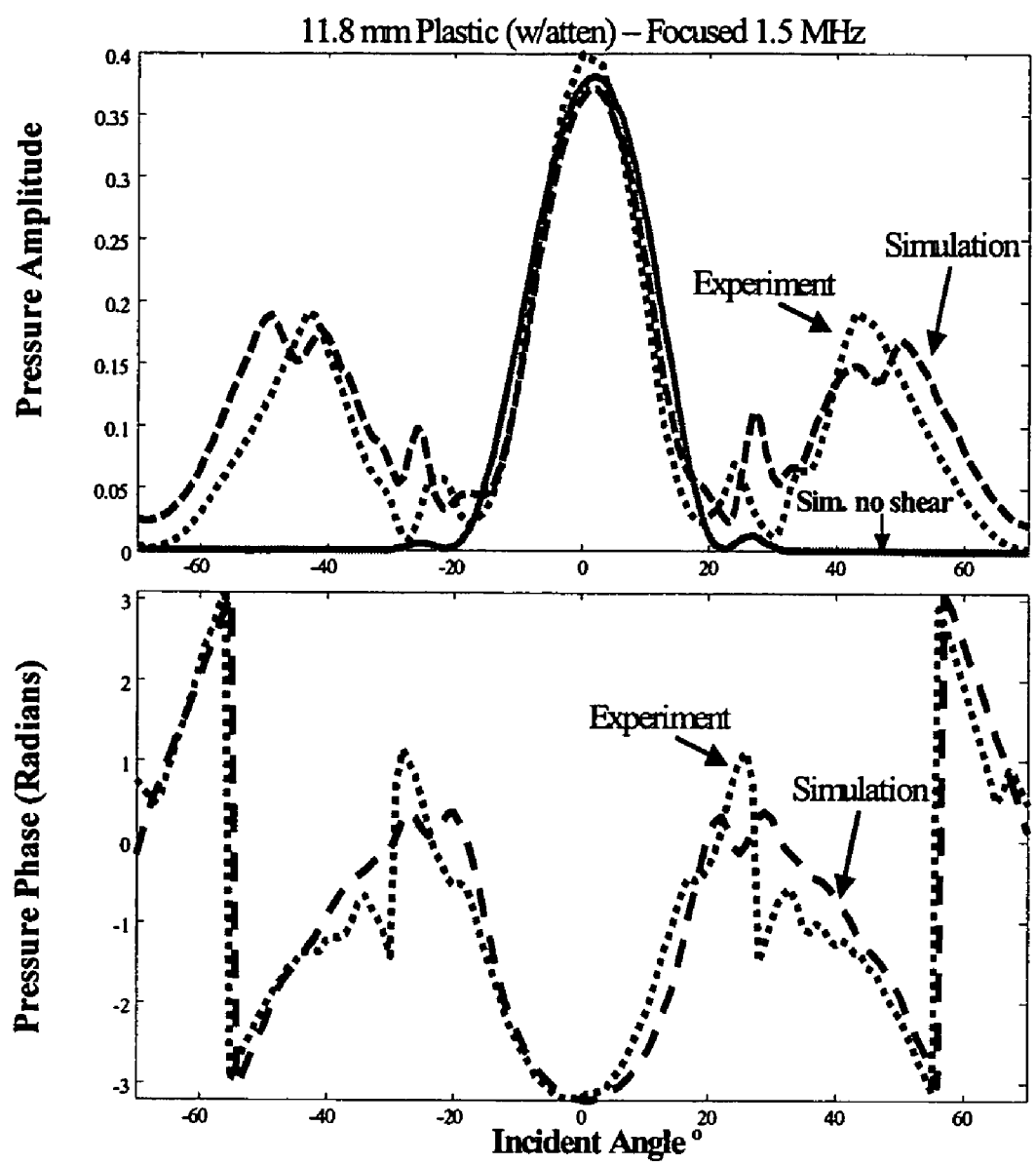
FIG. 13 is a pair of graphical representations of experimental and simulated pressure amplitude and phase as functions of incident angle.

The correlation between the measured and predicted fields is shown in FIG. 13. For reference, the plot also includes the amplitude of the numeric calculation obtained when shear waves were neglected. The amplitudes and phases of all three curves match closely for incident angles below 31°, which is the longitudinal critical angle for the signal's spectral peak. However, beyond this angle, the Longitudinal-only simulation is unable to predict the second local maxim in the amplitude, which results from a purely elastic wave within the sample. The major source of discrepancy between the measured data and simulation may be from result from underestimation of the shear wave absorption coefficient in the simulations. This effect becomes more pronounced at high angles, where the path length is longest. Very good correlation is found, however, between the simulated and measured ultrasound phase for all angles, with the exception of the transitional region between 20° and 30° where the wave amplitude is near its minimum. Neglecting this region, 76% of the remaining calculated points deviated from measurements by $\pi/6$, or less, radians.

Transskull Measurement

Figure 14A:
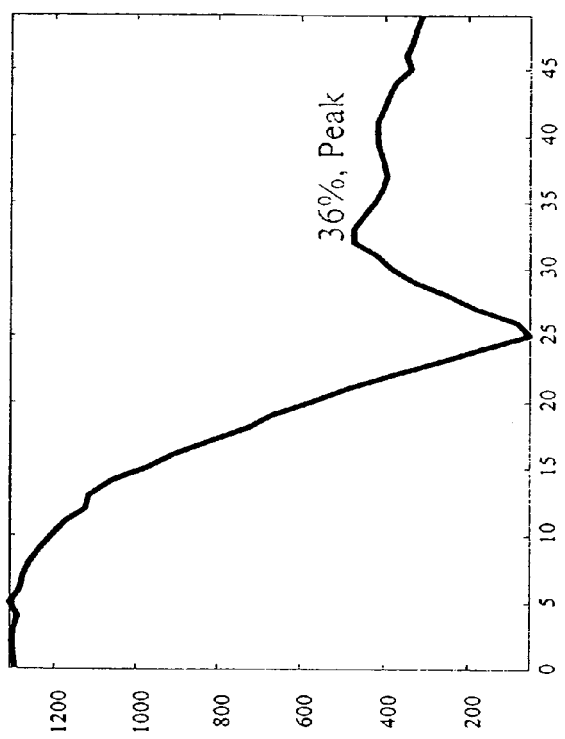
FIGS. 14A-B are plots of pressure amplitude and phase as a function of incident angle of a transskull experiment.
Figure 14B:
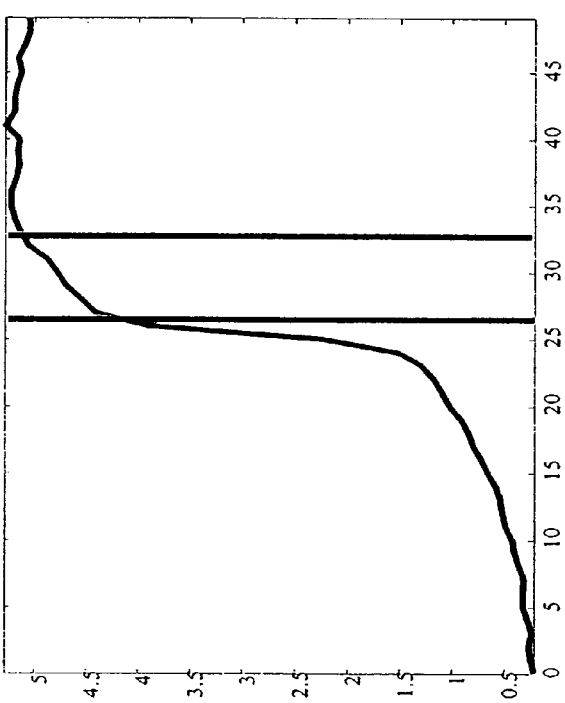

By rotating the skull, a local pressure transmission maximum was observed at 32°, which may result almost entirely from shear propagation through the bone, based on a longitudinal critical angle of about 30°. Further evidence of the wave's origin as a shear wave at higher incident angles was found in measured data shown in FIGS. 14A-B, that show the angular dependence of the wave phase. As shown in FIG. 14B, below 26° the phase closely resembles the behavior of a purely longitudinal wave. Between 26° and 32° there is a deceleration in the slope, indicating a region of superimposed contribution from the shear and longitudinal wave. Beyond 32° the slope approximately linear and negative since the shear sound speed is less than the speed of sound in water.

Figure 15:
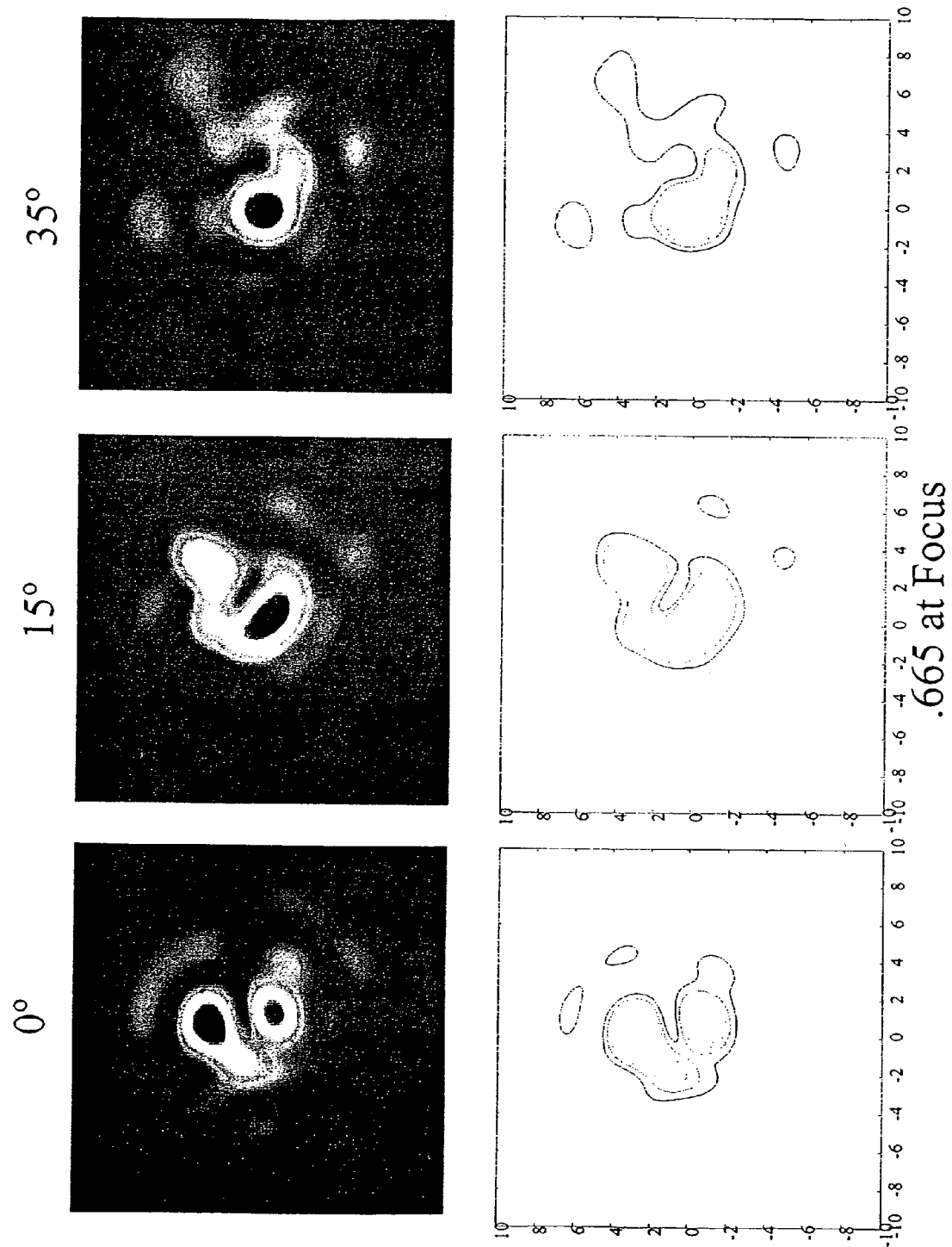
FIG. 15 are images of ultrasound transmitted through a skull at various incident angles.

Using the same mounting configuration, field measurements were performed over a 30 mm×30 mm area with 1 mm resolution, for different incident angles. FIG. 15 shows the field immediately after passing through the skull bone for incident angles of 0°, 15° and 35°, showing less distortion in the signal propagated through the skull as a shear wave than when propagated in a longitudinal mode at both 0° and 15°.

Figure 16:
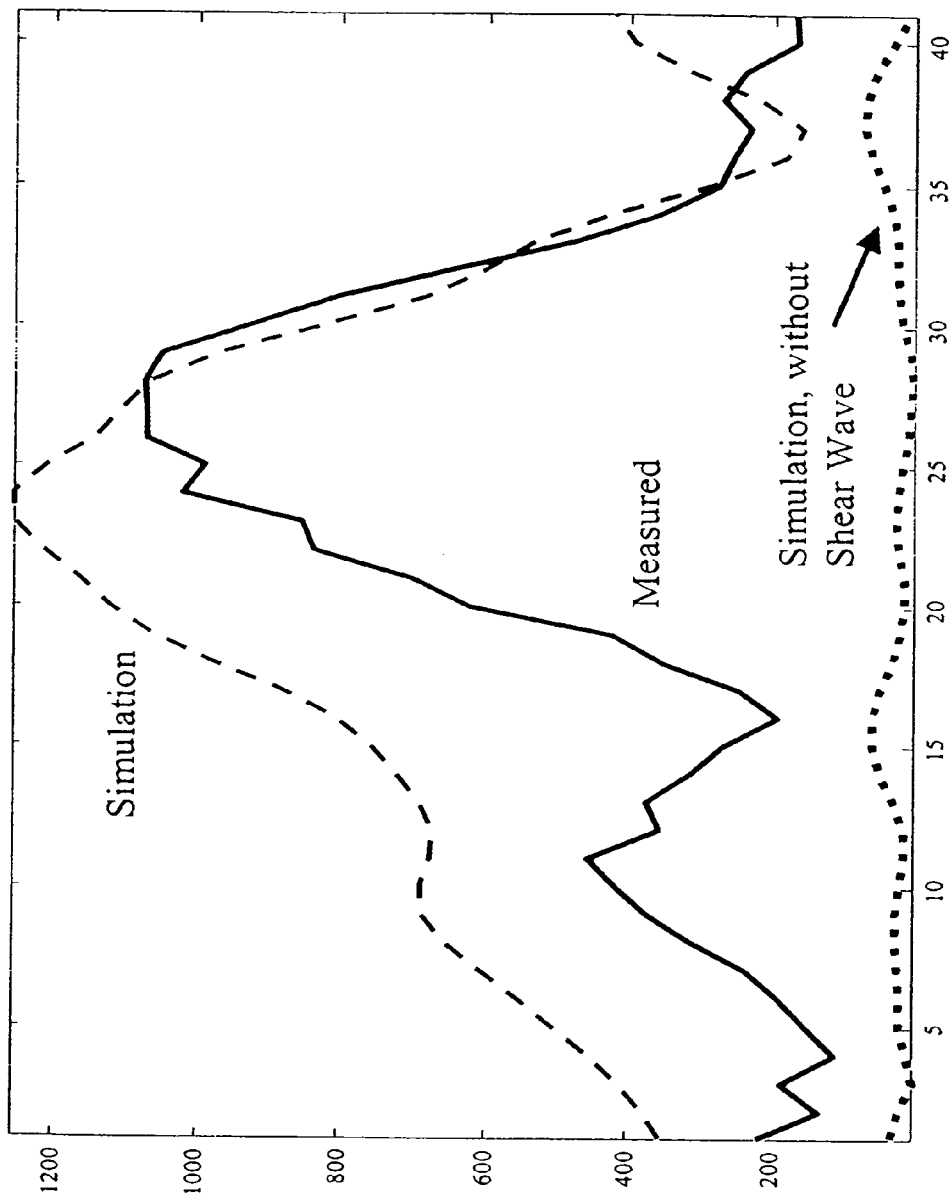
FIG. 16 is a plot of measured and simulated field measurements of ultrasound transmitted through a skull at a 32° incident angle.

A second set of measurements was performed with skulls placed in reference frames for spatial correlation with CT images. Although only an estimated value of the shear wave speed was used for the study, accurate spatial registration and data for the longitudinal modes allowed the longitudinal critical angle to be identified. Skulls were aligned to assure that the transmitted signal was from shear propagation in the bone. FIG. 16 shows an example where the outer surface of the skull is oriented at 32° relative to the axis of symmetry, as determined from the simulation algorithm. Although there is discrepancy between the simulation and the measurement, the simulation is able to identify the presence of the focused shear wave.

A demonstration was performed with a skull placed in a reference frame, to allow spatial correlation with CT images. Accurate spatial registration and data for the longitudinal modes allowed the longitudinal critical angle to be identified. Only an estimated value, however, of the shear wave speed was available for the study. Skulls were aligned to assure that the transmitted signal was from shear propagation in the bone. FIG. 7 shows a line measurement of the field, with the outer surface of the skull oriented at 32° relative to the axis of symmetry. Although there is discrepancy between the simulation and the measurement, the simulation was nonetheless able to identify the presence of the focused shear wave, with a beam shape resembling that of the measurement.

Diagnostic Applications—Transskull Imaging

For transskull imaging, the reflected signal propagates a second time back through the skull, returning with a measurable signal, preferably with little distortion. Signals were analyzed from a 1 MHz Panametrics imaging probe and pulse-receive amplifier. A nylon nut ($c=2.6\times10^6$ mm/s $Z=2.9$ M Rayl) served as the imaging object. The nut was suspended above the floor of a water tank by a thin steel needle. A-line images were acquired with the propagation direction first perpendicular to the skull and then at about 33°.

Figure 17A:
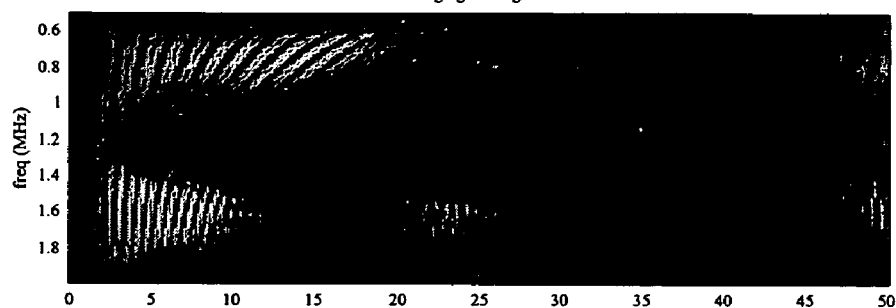
FIGS. 17A-B are images of non-normalized and normalized coded excitations.
Figure 17B:
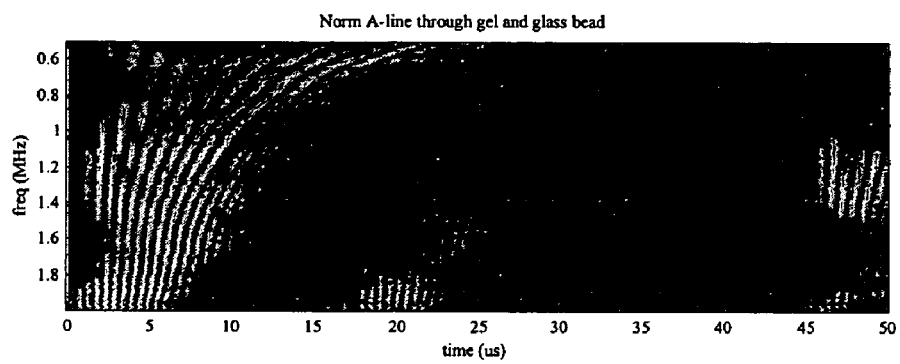
Figure 18A:
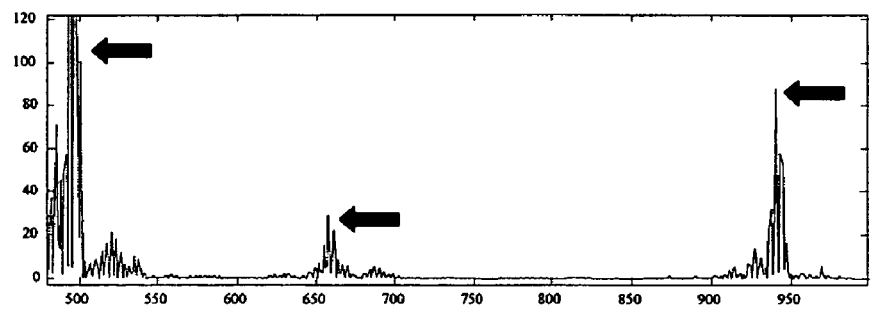
FIGS. 18A-B are plots of summed, filtered and unfiltered, respectively, transducer response to excitations shown in FIG. 17.
Figure 18B:
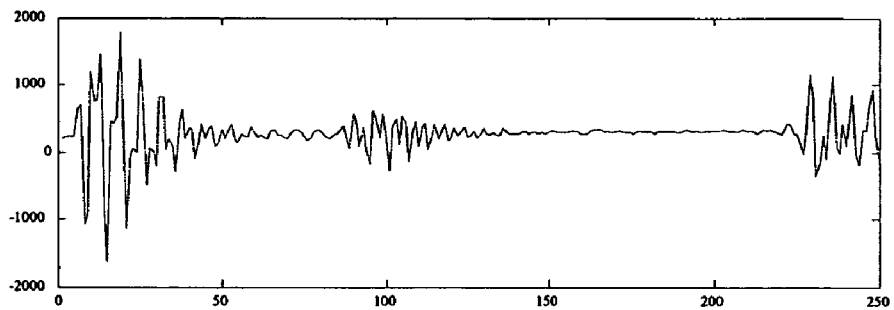

To help overcome losses, especially strong signal attenuation above 1 MHz, a new excitation scheme was used that sent a series of extended bursts through the skull. Bursts were repeated over a range of frequencies and the signals were numerically combined. In the exemplary experiment, 10 cycles were sent through the skull for frequencies ranging from 0.5 MHz to 2 MHz at 0.01 MHz intervals. This series of measurements is shown in FIG. 17A. The signals were then normalized by dividing by peak value to give even weight, to accentuate the weaker frequency signals as shown in FIG. 17B. Following acquisition, all of the time signals were summed and a matched filter was used to recover structural interfaces. The resulting signal is shown in FIG. 18A. This figure demonstrates significant improvement in localization and signal amplitude as compared with a single burst. Having a normalized spectrum across the frequency domain should allow better localization of interfaces after matched filtering is applied. Furthermore, forced driven oscillations of the transducer likely will increase the transducer's bandwidth at the high and low ends of its response. Also, the combined numeric signal will have a net power far exceeding powers that could safely be achieved with a single burst. Thus, significant improvement in the signal-to-noise ratio is likely.

Figure 19:
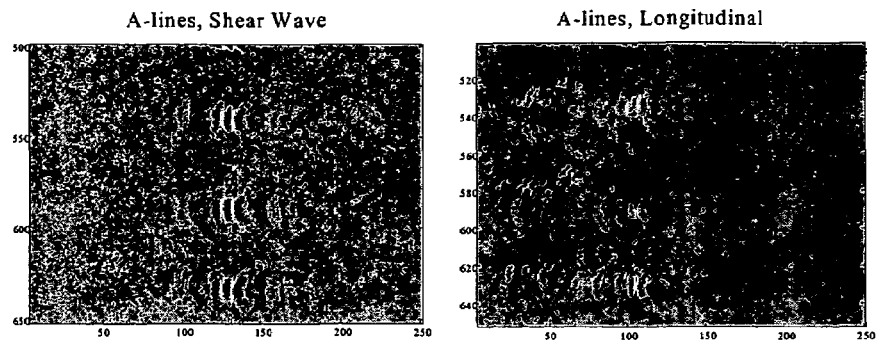
FIG. 19 shows A-line scans of shear waves and longitudinal waves.

The A-line images were followed by C-Scan imaging experiments using a focused broadband transducer array with a center frequency of 0.91 MHz. To construct the image, the 1 MHz transducer was affixed to a stepping motor positioner. The diameter of the transducer was 12.7 mm, representing the resolution limit of the present experiment. A scan of the nylon nut was obtained over a 20 mm×20 mm area first in water, then through a skull fragment at approximately normal incidence, and finally at an angle of approximately 33 degrees. The combination of axial (temporal) and radial information by beam steering allowed three-dimensional images to be constructed and evaluated. Image slices of the object are shown in FIG. 19 along lines of constant time. Spatial resolution of the image was limited by the diameter of the present imaging transducer, which detected backscattered data directly above the element.

A smaller beamwidth is expected to provide considerable improvement in image sharpness. Distortion between the water scan and the transcranial scan is at least in part caused by the method of image acquisition procedure. The act of moving the transducer over the skull surface introduced additional distortion due to the spatial variation of the skull thickness and acoustic properties. Aberration correction may be unnecessary in cases where a narrow ultrasound beam is directed through the skull. If a larger area array is used, however, noninvasive aberration correction algorithms could be employed.

Noninvasive phase aberration correction could also be used to restore the focus through the skull bone. In this case, phase distortion could be predicted using carefully registered information from CT scans of the ex vivo skulls. However, with the imaging hardware it is also possible that the overall phase distortion can be predicted from signature reflections off of the base of the skull. The reflection point would serve as a virtual transmitter in the brain and could be used for focusing at any point in the brain. Success with this method could improve focusing and potentially eliminate the need for CT scans of the head. In practice, a transducer array with a center frequency between about 0.5 MHz and about 2 MHz and with at least 100 elements may be used to help assure ample beam steering ability.

Figure 20:
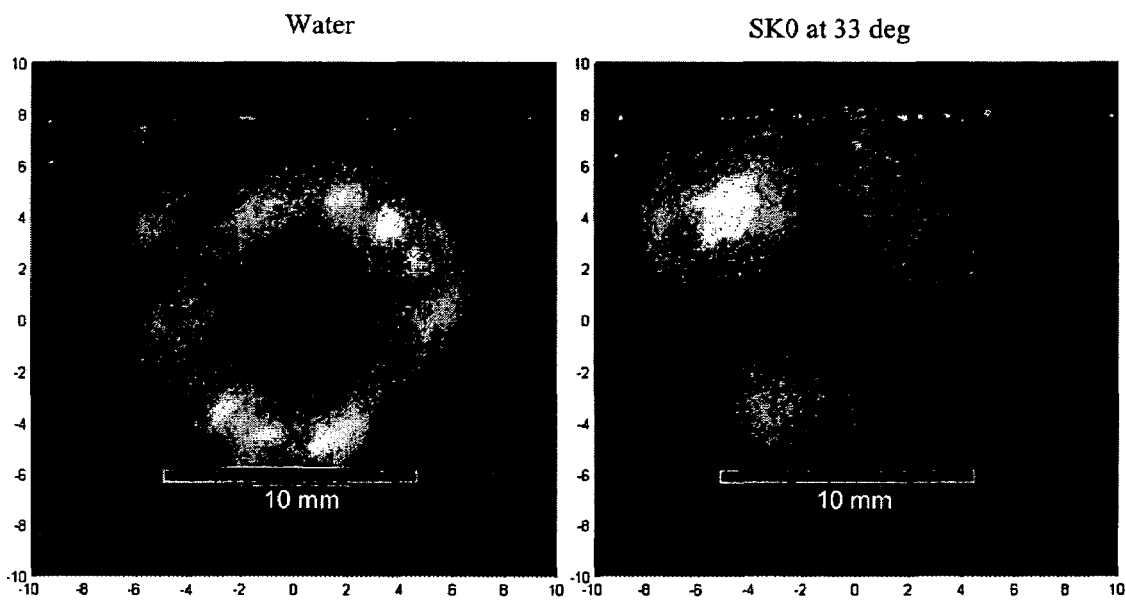
FIG. 20 shows images of a nylon nut at 0° and 33° incident angle through skull.

Improvements in the signal could be quantified in terms of SNR as well as measurements of the reduction in object distortion and the accuracy of object locations. The apparatus setup (e.g., that shown in FIG. 2) preferably uses a fast switching multiplexer to allow waveforms to be recorded from multiple channels across the array. A comparison of the images at 0 degrees incidence and 33 degrees is presented in FIG. 20, showing a reduction in the image noise at 33 degrees.

Diagnostic Applications—Cavity Imaging

Figure 21:
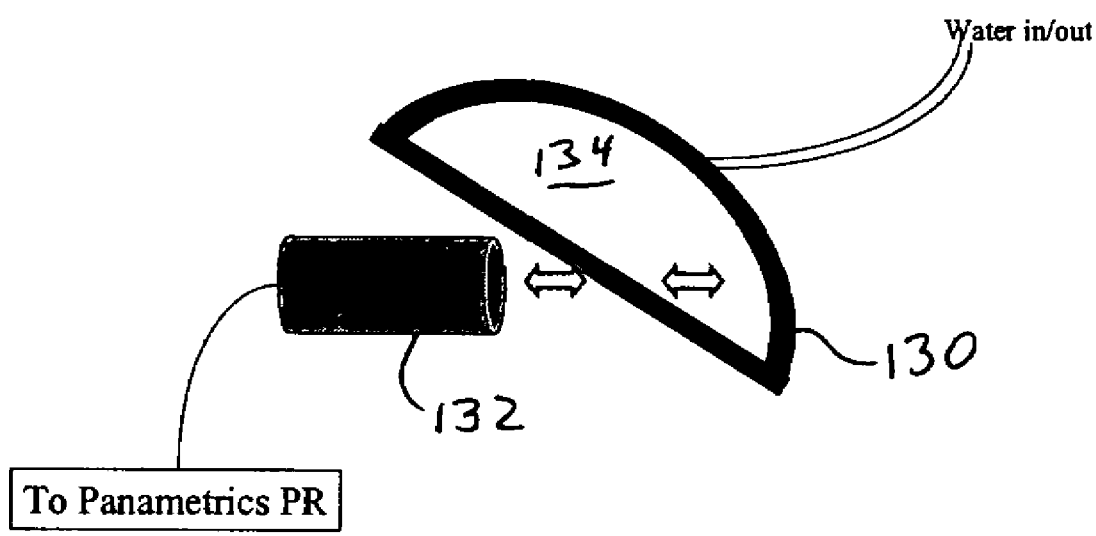
FIG. 21 is a schematic diagram of an experimental setup for testing cavity imaging using shear wave propagation of ultrasound.

Application of the transskull method may be used in applications not only for the brain, but also for the sinus cavities within the skull, that fill with fluid when infected. Referring to FIG. 21, to demonstrate applicability, a plastic phantom 130 was developed that provided a cavity 134 that could be filled with fluid (water) and drained. A 1-MHz center frequency Panametrics transducer 132 was pulsed in order to send a signal through the phantom 130 in one of four situations: (1) A high angle of ultrasound incidence (>45°) to induce shear wave propagation through the phantom 130 with an the cavity 134 being air filled; (2) A high angle of ultrasound incidence with a the cavity 134 being water filled; (3) A low angle of ultrasound incidence (<5°) giving nearly all longitudinal wave propagation through the phantom 130 with the cavity 134 being air filled; and (4) A low incidence angle with the cavity 134 being water filled.

Figure 22A:
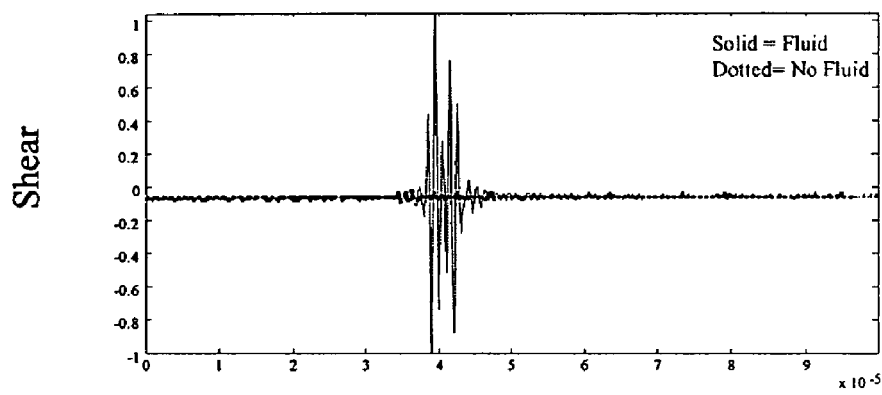
FIGS. 22A-B are plots of responses to shear waves and longitudinal waves, respectively, incident upon water-filled and air-filled cavities.
Figure 22B:
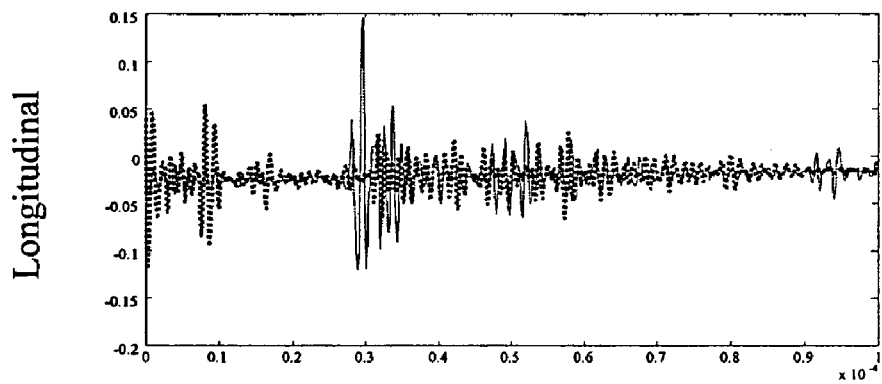

An example of advantages for cavity imaging using shear waves is presented in the results of the experiments shown in FIGS. 22A-B. FIG. 22A shows a dramatic difference in the time history of the high angle signal when the cavity is air filled, and when it is fluid filled. In contrast, the longitudinal results shown in FIG. 22B are complicated in both the air and fluid filled cases by additional signal information coming from reflections within the bone itself, making accurate diagnosis of the imaging situation difficult. These results suggest that in practice, the shear mode could have clinical application as a method of determining the presence of fluid in sinuses.

DISCUSSION

Preliminary simulations and experimental measurements indicated that a coherent, focused ultrasound beam can be transmitted through the skull as a purely shear wave. At a driving frequency near 0.7 MHz, the peak amplitude through the skull due to shear propagation in the bone was found to be on the order of, and sometimes higher than, longitudinal propagation. Furthermore, the fact that the shear wave experienced a reduced overall phase shift confirms the viability of simplifying and extending noninvasive transskull focusing methods to a larger region in the brain. Although the shear amplitude was lower than longitudinal modes, there was evidence that the overall beam may suffer less distortion when propagated through a localized region of the bone. Furthermore, the shear mode experienced less phase distortion, presumably due to the similarity between the shear wave speed and the speed of sound in water. Comparable similarities would be found in soft tissues. More precise correlation between the simulation and measured data may be obtained using a more accurate measurement of the shear wave speed in the skull bone.

There are several possible direct implications of intentionally using shear waves in transskull applications (although the invention is not limited to this application. First, shear wave propagation may be added to pre-existing non-invasive transskull phasing algorithms for improved focusing at high incident angles. This is particularly important when focusing close to the skull surface, where high angular incidence is used. Second, shear wave propagation may have application in transskull imaging, where a narrow ultrasound beam would be directed through the skull at intentionally high incident angles. Third, shear wave propagation could potentially be used to detect flow in the brain by means of frequency Doppler shifts. All of these techniques may be performed in the sub-megahertz frequency range discussed.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. Further, if different pulses are used having different frequencies and amplitudes, each of the pulses need not have only one frequency and one amplitude; one or more of the pulses may have more than one frequency and/or amplitude. Also, incident ultrasound energy need not be directed at a subject above the longitudinal critical angle in order to induce shear waves. The incident angle could be below Snell's angle, e.g., normal to the surface of the subject and/or the subject's bone. It is, however, preferred to direct the energy to be incident at an angle between the longitudinal and shear wave critical angles as this may help produce a desired amount of shear wave energy.

APPENDIX A

The pressure amplitudes were calculated by solving for the velocity potentials described in Eqns. (1), (2), (3) and (8). After linear algebraic simultaneous solution of the equations, it may be shown that the shear and longitudinal wave amplitudes in the bone are given by.

$$A_S^{II}(\theta^I) = \frac{-4A_L^I c^{I2} k^{I2} k_L^{II} \rho^I \cos\theta^I \cos\theta_L^{II} \sin\theta_L^{II} / k_s^{II}}{D_{II}(\theta^I)\rho^{II}\cos\theta^I + c_{II}^2 k^I \rho^I C_{II}(\theta^I)} \quad (9)$$

and $$A_L^{II}(\theta^I) = \frac{2A_L^I c^{I2} k^{I2} k_S^{II} \rho^I \cos\theta^I \cos2\theta_S^{II} / k_L^{II}}{D_{II}(\theta^I)\rho^{II}\cos\theta^I + c^{II2} k^I \rho^I \cos\theta_L B_{II}(\theta^I)} \quad (10)$$

where, $$B_{II}(\theta^I) = k_S^{II} \cos 2\theta_S^{II} + 2k_L^{II} \sin \theta_L^{II} \sin \theta_S^{II}, \quad (11)$$

$$C_{II}(\theta^I) = k_S \cos\theta_L^{II} \cos 2\theta_S^{II} + k_L \sin 2\theta_S^{II} \sin \theta_S^{II}, \quad (12)$$

$$D_{II}(\theta^I) = k_L^{II} k_S^{II} (c_L^{II2} \cos 2\theta_S^{II} - 2c_S^{II2} \sin \theta_L^{II} \sin(\theta_L^{II} - 2\theta_S^{II})), \quad (13)$$

and the transmitted angles are understood to be functions of θ, related by Snell's Law, $$\frac{\sin\theta^I}{c^I} = \frac{\sin\theta_L^{II}}{c_L^{II}} = \frac{\sin\theta_S^{II}}{c_S^{II}}. \quad (14)$$

The amplitudes of the waves transmitted into the brain from the incident longitudinal and shear waves are equal to $$A_{LS}^{III}(\theta^I) = \frac{-(2A_S^{II}(\theta^I)c_S^2 k_S^2 \rho_{sk} \cos\theta_L^{III})}{D(\theta^I)\rho^{II}\cos\theta^{III} + c^{III2} k^{III} \rho^{III} C_{II}(\theta^I)} \quad (15)$$

and $$A_{LL}^{III}(\theta^I) = \frac{2A_L^{II}(\theta^I) k_L^{II2} \rho^{II} \cos\theta_L (c_L^{II2} - c_S^{II2} + c_S^{II2} \cos2\theta_L^{II})}{\rho^{II}\cos\theta^{III} D_{II}(\theta^I) + c^{III2} k^{III} \rho^{III} \cos\theta_L^{II} B_{II}(\theta^I)}. \quad (16)$$

Appendix B

Regardless of whether or not the layers are parallel, the transfer function may still be written in a closed form. For the thickness across the z-axis, $z_n$, the sound speed $c_n$, and density of each layer (n=I, II, III), that the unit vectors normal to the layer surfaces $\hat{n}_n$ is calculated. For a given initial wavevector $\vec{k}_{0xy}$, the ray path from (0,0, $z_0$) between any two surface interfaces traverses a distance of $$|\vec{R}_{nxy}| = \frac{(\vec{z}_{nxy} - \vec{r}_{nxy}) \cdot \hat{n}_{n+1}}{\hat{k}_{nxy} \cdot \hat{n}_{n+1}}, \quad (17)$$

where, as depicted in FIG. 2, $\vec{r}_{nxy}$ is the vector extending along the layer from z-axis to the intercept of the layer with the ray. The unit vector along the wavevector's path is given by $\hat{k}_{nxy}$. Again, the frequency dependence on the wavevector orientation is understood. It follows that the ray position vector must be equal to $\vec{R}_{nxy} = |\vec{R}_{nxy}|\hat{k}_{nxy}$. Although the initial wavevector orientation, $\hat{k}_{0xy}$, is known, the direction of the wave vector in the first and subsequent layers must be calculated using the relation $$\frac{1}{c_n}(\hat{n}_{n+1} + \hat{k}_{nxy}) = \frac{1}{c_{n+1}}(\hat{n}_{n+1} \times \hat{k}_{n+1xy}), \quad (18)$$

which is a consequence of Snell's law in three dimensional space that requires the incident wavevector, the transmitted wavevector and the normal vector all be in the same plane. The transmitted wavevector on the right hand side of Eq. (18) may be obtained by crossing both sides of the equation with $\hat{n}_{n+1}$. Using cross product relations, it may be shown that $$\hat{k}_{n+1xy} = \frac{c_{n+1}}{c_n}(\hat{k}_{nxy} - \cos\gamma_{i_{n+1xy}}\hat{n}_{n+1}) + \cos\gamma_{i_{n+1xy}}\hat{n}_{n+1} \quad (19)$$

The incident unit wavevector of the $n^{th}$ layer is equal to the transmitted wave of the $(n-1)^{st}$ layer. With the exception of the $0^{th}$ layer shown in FIG. 2, $\vec{r}_{nxy}$ is found in order to calculate Eq. (17). Given the thickness across the z-axis of each layer, the point of intersection of ray $\vec{R}_n$ with the surface of the n+1 layer is $$\vec{r}_{n+1} = \vec{R}_n + \vec{r}_n - \vec{z}_n. \quad (20)$$

Over a series of N layers, the phase of a ray reaching the $N^{th}$ plane $\phi_R(\vec{k}_{Nxy},\omega)$ is the sum of the phase contributions over each path length given by Eq.(17). The spatial phase at the plane z, is related to the ray phase at N by $\phi_N(\vec{k}_{Nxy},\omega)=\phi_R(\vec{k}_{Nxy},\omega)-2\pi k_N r_N \sin \gamma_{Nxy}$, as illustrated in FIG. 2. A ray leaving the initial plane with a polar angle $\gamma_{0xy}(\omega)$ will arrive at the plane z with a new orientation $\gamma_{Nxy}(\omega)$ determined by the N−1 unit vector $\hat{k}_{N-1}$.

$$\phi(\vec{k}_{Nxy},\omega,z) = \phi(\vec{k}_{0xy},\omega,z_0) + \sum_{n=0}^{N-1} k_n \frac{(\vec{z}_n - \vec{r}_n)\cdot \hat{n}_{n+1}}{\hat{k}_n \cdot \hat{n}_{n+1}} - \sin\gamma_{Nxy}(\omega), \quad (21)$$

given $\phi(\vec{k}_{0xy},\omega,z_0)$, the phase of $\tilde{p}(k_x,k_y,\omega,z_0)$ at the initial plane.

The pressure over the plane at z can be expressed in terms of the ray phase presented in Eq. (21) and the transmission coefficient given in $$\tilde{p}(\vec{k}_{Nxy},\omega,z) = \tilde{p}(\vec{k}_{0xy},\omega,z_0)e^{-i\sin\gamma_{Nxy}(\omega)}\left[\prod_{n=1}^{N-1} T_{nxy}(\omega)e^{i\phi_N(\vec{k}_{Nxy},\omega,z)}\right], \quad (22)$$

where the terms in square brackets on the right hand side of Eq. (22) can be viewed as an operator that maps the field from $k_0$-space to a new $k_N$-space. In the present problem, the amplitudes, T, are given by to Eqns. (15) and (16) and the component angles, $\gamma_{Nxy}$. In practice, this mapping requires interpolation to produce a linearly spaced matrix at z.

What is claimed is:

1. A method of delivering ultrasound signals using shear waves, the method comprising applying first longitudinal waves of at least a first ultrasound beam to a subject at at least a first incident angle relative to a first surface of the subject such that the first longitudinal waves are converted to first shear waves in the subject and are converted to second longitudinal waves at a second surface of the subject, energy in the second longitudinal waves forming a substantial part of energy of ultrasound waves at a desired region in the subject at a therapeutic level.

2. The method of claim 1 wherein the first longitudinal waves are applied to a surface of the subject between a longitudinal wave critical angle associated with the subject and a shear wave critical angle associated with the subject.

3. The method of claim 1 wherein applying the first longitudinal waves comprises applying ultrasound energy at multiple incident angles between the longitudinal wave critical angle associated with the subject and the shear wave critical angle associated with the subject to focus ultrasound energy in the desired region.

4. The method of claim 1 wherein applying the first longitudinal waves comprises applying the first longitudinal waves to bone.

5. The method of claim 4 wherein the bone is a skull, and wherein the first longitudinal waves directed at the skull at the at least a first incident angle in order to reach the desired region within the skull.

6. The method of claim 1 wherein the first longitudinal waves are applied in multiple bursts of different frequencies.

7. The method of claim 6 wherein the different frequencies are within a range of frequencies from about 0.1 MHz and about 5 MHz.

8. The method of claim 6 wherein the different frequencies are within a range of frequencies from about 0.2 MHz and about 3 MHz.

9. The method of claim 6 wherein the pulses have durations within a range of about 1 cycle to continuous wave.

10. The method of claim 1 wherein applying the first longitudinal waves comprises applying third longitudinal waves to the subject to produce second shear waves in the subject to produce fourth longitudinal waves in the desired region.

11. The method of claim 10 wherein the third longitudinal waves are separate from the first longitudinal waves.

12. The method of claim 1 wherein applying the first longitudinal waves comprises applying fifth longitudinal waves to the subject at a second incident angle that is less than the longitudinal wave critical angle associated with the subject.

13. A system for delivering ultrasound signals to a target region in a subject using shear waves, the system comprising:
a source configured to transmit ultrasound energy; and
directing means, coupled to the source, for causing at least first longitudinal waves of the transmitted ultrasound energy to be incident upon a surface of the subject the first longitudinal waves are converted to first shear waves in the subject and are converted to second longitudinal waves at a second surface of the subject, energy in the second longitudinal waves forming a substantial part of energy of ultrasound waves at the target region in the subject at a therapeutic level.

14. The system of claim 13 wherein the directing means is configured to direct the first longitudinal waves at the surface of the subject at a first angle between a longitudinal critical angle associated with the subject and a shear critical angle associated with the subject.

15. The system of claim 14 wherein the directing means comprises at least one of (1) a positioner configured to mechanically direct a normal direction associated with the source toward the surface at the first angle, and (2) a phase/delay adjuster, wherein the source comprises a plurality of radiating elements, the phase/delay adjuster being configured to regulate at least one of phases and delays of the plurality of radiating elements to electronically steer at least the first longitudinal waves.

16. The system of claim 15 wherein the positioner is configured to at least one of (1) couple to the subject and the source in a fixed manner such that the normal is directed toward the surface at the first angle, and (2) mechanically adjust the source such that the normal is directed toward the surface at the first angle.

17. The system of claim 15 wherein the source comprises a plurality of elements configured to radiate ultrasound energy, the system comprising a controller configured and coupled to cause at least a portion of the source to emit ultrasound energy, to process indicia of reflected energy due to the emitted energy to determine an orientation of at least a portion of the surface relative to the source, and to actuate only elements of the source that have their mainbeams at least partially directed at the portion of the surface between the longitudinal critical angle and the shear wave critical angle.

18. The system of claim 14 comprising a controller coupled to the source and configured to actuate the source to produce the first longitudinal waves and third longitudinal waves incident upon a surface of the subject at a second angle between the longitudinal critical angle associated with the subject and the shear critical angle associated with the subject such that ultrasound energy in the third longitudinal waves will induce second shear waves in the subject that will be converted to fourth longitudinal waves that will reach target region, wherein the second angle is different from the first angle.

19. The system of claim 13 comprising a controller coupled to the source and configured to actuate the source to produce the first longitudinal waves for transmitting energy to the target region.

20. The system of claim 13 comprising a controller coupled to the source and configured to actuate the source to produce the first longitudinal waves in a plurality of pulses with different frequencies.

21. The system of claim 20 wherein the different frequencies are within a range of frequencies from about 0.1 MHz and about 5 MHz.

22. The system of claim 21 wherein the different frequencies are within a range of frequencies from about 0.2 MHz and about 3 MHz.

23. The system of claim 20 wherein the pulses have durations within a range of about 1 cycle to continuous wave.

24. The system of claim 13 comprising a controller coupled to the source and configured to actuate the source to produce the first longitudinal waves and fifth longitudinal waves incident upon a surface of the subject at a third angle that is less than the longitudinal critical angle associated with the subject.

25. A system for delivering ultrasound signals to a target region in a subject using shear waves, the system comprising:
 a source configured to transmit ultrasound energy;
 a controller coupled to the source and configured to actuate the source to transmit ultrasound energy toward the subject; and
 a positioning device coupled to the source and configured to ensure that first longitudinal waves of a first mainbeam from at least a portion of the source is directed at a portion of a first surface of the subject at a first angle between a longitudinal critical angle associated with the subject and a shear critical angle associated with the subject such that the first longitudinal waves are converted to shear waves in the subject and are converted to second longitudinal waves at a second surface of the subject and energy from the second longitudinal waves will reach the target region;
 wherein the controller is configured to cause the source to transmit energy in a plurality of pulses, with each pulse having a different frequency.

26. The system of claim 25 wherein the source comprises a plurality of elements configured to transmit ultrasound energy, and wherein the controller is configured to inhibit actuation of at least one of (1) a portion of the source configured to produce a second mainbeam at least a portion of which would be incident upon the portion of the first surface of the subject at a second angle that is less than the longitudinal critical angle, and (2) a portion of the source configured to produce a third mainbeam at least a portion of which would be incident upon the portion of the first surface of the subject at a third angle that is greater than the shear wave critical angle.

27. The system of claim 25 wherein the different frequencies are within a range of frequencies from about 0.1 MHz and about 5 MHz.

28. The system of claim 27 wherein the different frequencies are within a range of frequencies from about 0.2 MHz and about 3 MHz.

29. The system of claim 27 wherein the pulses have durations within a range of about 1 cycle to continuous wave.

30. The system of claim 25 wherein the positioning device is configured to couple to the subject to mechanically orient the source relative to the subject as desired.

31. The system of claim 25 wherein the source comprises a plurality of elements configured to transmit ultrasound energy, and wherein the positioning device is configured to affect phases of the elements to electronically steer the first mainbeam.

* * * * *